(12) United States Patent
Allen et al.

(10) Patent No.: US 12,163,117 B2
(45) Date of Patent: Dec. 10, 2024

(54) BIOREACTOR CHAMBER AND SYSTEMS THEREOF

(71) Applicant: University of Florida Research Foundation, Inc., Gainesville, FL (US)

(72) Inventors: Josephine Allen, Gainesville, FL (US); Bryan D. James, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 682 days.

(21) Appl. No.: 17/423,303

(22) PCT Filed: Jan. 10, 2020

(86) PCT No.: PCT/US2020/013177
§ 371 (c)(1),
(2) Date: Jul. 15, 2021

(87) PCT Pub. No.: WO2020/150107
PCT Pub. Date: Jul. 23, 2020

(65) Prior Publication Data
US 2022/0235309 A1 Jul. 28, 2022

Related U.S. Application Data

(60) Provisional application No. 62/793,264, filed on Jan. 16, 2019.

(51) Int. Cl.
*C12M 1/42* (2006.01)
*C12M 1/00* (2006.01)
*C12M 1/12* (2006.01)

(52) U.S. Cl.
CPC ............ *C12M 35/04* (2013.01); *C12M 23/04* (2013.01); *C12M 23/22* (2013.01); *C12M 23/26* (2013.01); *C12M 25/14* (2013.01)

(58) Field of Classification Search
CPC ...... C12M 35/04; C12M 23/04; C12M 23/22; C12M 23/26; C12M 25/14; C12M 29/00; C12M 41/00
See application file for complete search history.

(56) References Cited

U.S. PATENT DOCUMENTS 5,153,136 A * 10/1992 Vandenburgh ....... C12N 5/0062
435/305.3
6,107,081 A 8/2000 Feeback
(Continued)

FOREIGN PATENT DOCUMENTS

| EP | 1 077 072 B1 | 11/2003 |
| EP | 2 236 597 A1 | 10/2010 |

(Continued)

OTHER PUBLICATIONS

International Search Report and Written Opinion for PCT /US2020/013177 mailed on Apr. 14, 2020.
(Continued)

*Primary Examiner* — William H. Beisner
*Assistant Examiner* — Danielle B Henkel
(74) *Attorney, Agent, or Firm* — Thomas | Horstemeyer, LLP

(57) ABSTRACT

Described herein are bioreactor chambers and systems thereof. In an embodiment, a single-plate symmetrical bioreactor chamber is described, comprising: a flow channel extending along a first axis, wherein the flow channel comprises an inlet and an outlet at opposing ends of 5 the flow channel; a pair of struts on opposing ends of a second axis, wherein the second axis is substantially perpendicular to the first axis, wherein each strut of the pair of struts are placed on opposing sides of the flow channel, wherein the struts are configured to be coupled to a bidirectional linear actuator and configured to provide a strain perpendicular to
(Continued)

a fluid flow through the flow channel, wherein the strain does not laterally displace cells present in the flow channel.

19 Claims, 31 Drawing Sheets

(56) References Cited

U.S. PATENT DOCUMENTS

| | | | |
|---|---|---|---|
| 7,547,540 | B2 | 6/2009 | Takagi et al. |
| 7,906,322 | B2* | 3/2011 | Bergeron .............. C12M 35/04 435/284.1 |
| 9,803,167 | B2 | 10/2017 | Choi et al. |
| 2004/0219659 | A1 | 11/2004 | Altman |
| 2004/0235153 | A1* | 11/2004 | Takagi .................. C12M 35/04 435/293.2 |
| 2006/0068492 | A1 | 3/2006 | Choi |
| 2008/0274545 | A1 | 11/2008 | Kuo |
| 2012/0034695 | A1 | 2/2012 | Sethu |

FOREIGN PATENT DOCUMENTS

| | | |
|---|---|---|
| JP | 2006-000105 A | 1/2006 |
| WO | 2005123258 A1 | 12/2005 |

OTHER PUBLICATIONS

James et al., A Decoupled Multi-Stimulus Bioreactor for Studying Complex Chemo-Mechanical , Microenvironments In Vitro, Society for Biomaterials Annual Meeting and Exposition 2019.
Sinha, Ravi et al. "Endothelial cell alignment as a result of anisotropic strain and flow induced shear stress combinations." Scientific reports vol. 6 29510. Jul. 12, 2016, doi: 10.1038/srep29510.
Peng, X et al. "In vitro system to study realistic pulsatile flow and stretch signaling in cultured vascular cells." American journal of physiology. Cell physiology vol. 279,3 (2000): C797-805. doi: 10.1152/ajpcell.2000.279.3.C797.
Debbi, Lior et al. "The Influence of the Timing of Cyclic Load Application on Cardiac Cell Contraction." Frontiers in physiology vol. 9 917. Jul. 18, 2018, doi: 10.3389/fphys.2018.00917.
Nakadate et al, "A New in Vitro Pulsatile Perfusion System that Mimics Physiological Transmural Pressure and Shear Stress in Any Size of in Vivo Vessel", journal of Biomechanical Science and Engineering, vol. 3 No. 1, 2008, pp. 25-37.
Spruell, Christopher, "Analysis of a high-throughput cone-and-plate apparatus for the application of defined spatiotemporal flow to cultured cells." Biotechnology and bioengineering vol. 110,6 (2013): 1782-93. doi:10.1002/bit.24823.
Estrada, Rosendo et al. "Microfluidic endothelial cell culture model to replicate disturbed flow conditions seen in atherosclerosis susceptible regions." Biomicrofluidics vol. 5,3 (2011): 32006-3200611. doi: 10.1063/1.3608137.
Tse, Justin R, and Adam J Engler. "Preparation of hydrogel substrates with tunable mechanical properties." Current protocols in cell biology vol. Chapter 10 (2010): Unit 10.16. doi:10.1002/0471143030.cb1016s47.
Feinberg, Adam W et al. "Systematic variation of microtopography, surface chemistry and elastic modulus and the state dependent effect on endothelial cell alignment." Journal of biomedical materials research. Part A vol. 86,2 (2008): 522-34. doi:10.1002/jbm.a.31626.
Li, Bin et al. "RGD peptide-conjugated poly(dimethylsiloxane) promotes adhesion, proliferation, and collagen secretion of human fibroblasts." Journal of biomedical materials research. Part A vol. 79,4 (2006): 989-98. doi: 10.1002/jbm.a.30847.
Sinha, Ravi et al. "Tuning Cell and Tissue Development by Combining Multiple Mechanical Signals." Tissue engineering. Part B, Reviews vol. 23,5 (2017): 494-504. doi:10.1089/ten.TEB.2016.0500.

Toepke, Michael W, and David J Beebe. "PDMS absorption of small molecules and consequences in microfluidic applications." Lab on a chip vol. 6,12 (2006): 1484-6. doi:10.1039/b612140c.
Yamamura, Nahoko et al. "Effects of the mechanical properties of collagen gel on the in vitro formation of microvessel networks by endothelial cells." Tissue engineering vol. 13,7 (2007): 1443-53. doi: 10.1089/ten.2006.0333.
Paluch, E. K.; Nelson, C. M.; Biais, N.; Fabry, B.; Moeller, J.; Pruitt, B. L.; Wollnik, C.; Kudryasheva, G.; Rehfeldt, F.; Federle, W., "Mechanotransduction: Use the Force(S)"., BMC Biol. 2015, 13 (1), 1-14. https://doi.org/10.1186/s12915-015-0150-4.
Chiu, J.-J.; Chien, S., "Effects of Disturbed Flow on Vascular Endothelium: Pathophysiological Basis and Clinical Perspectives",. Physiol. Rev. 2011, 91 (1), 327-387. https://doi.org/10.1152/physrev.00047.2009.
James, B. D.; Allen, J. B., "Vascular Endothelial Cell Behavior in Complex Mechanical Microenvironments"., ACS Biomater. Sci. Eng. 2018, 4 (11), 3818-3842. https://doi.org/10.1021/acsbiomaterials.8b00628.
Jufri, N. F.; Mohamedali, A.; Avolio, A.; Baker, M. S., "Mechanical Stretch: Physiological and Pathological Implications for Human Vascular Endothelial Cells"., Vasc. Cell 2015, 7 (1), 8. https://doi.org/10.1186/s13221-015-0033-z.
Yang, C.; Tibbitt, M. W.; Basta, L.; Anseth, K. S., "Mechanical Memory and Dosing Influence Stem Cell Fate"., Nat. Mater. 2014, 13 (6), 645-652. https://doi.org/10.1038/nmat3889.
Chaudhuri, O.; Gu, L.; Klumpers, D.; Darnell, M.; Bencherif, S. A.; Weaver, J. C.; Huebsch, N.; Lee, H. P.; Lippens, E.; Duda, G. N.; et al., "Hydrogels with Tunable Stress Relaxation Regulate Stem Cell Fate and Activity"., Nat. Mater. 2016, 15 (3), 326-334. https://doi.org/10.1038/nmat4489.
Levental, I.; Georges, P. C.; Janmey, P. A., "Soft Biological Materials and Their Impact on Cell Function",. Soft Matter 2007, 3 (3), 299-306. https://doi.org/10.1039/B610522J.
Greiner, A. M.; Sales, A.; Chen, H.; Biela, S. A.; Kaufmann, D.; Kemkemer, R., "Nano- and Microstructured Materials for in Vitro Studies of the Physiology of Vascular Cells",. Beilstein J. Nanotechnol. 2016, 7, 1620-1641. https://doi.org/10.3762/bjnano.7.155.
Estrada, R.; Giridharan, G. A.; Nguyen, M.-D.; Roussel, T. J.; Shakeri, M.; Parichehreh, V.; Prabhu, S. D.; Sethu, P., "Endothelial Cell Culture Model for Replication of Physiological Profiles of Pressure, Flow, Stretch, and Shear Stress in Vitro",. Anal. Chem. 2011, 83 (8), 3170-3177. https://doi.org/10.1021/ac2002998.
Huh, D.; Matthews, B. D.; Mammoto, A.; Montoya-Zavala, M.; Hsin, H. Y.; Ingber, D. E., "Reconstituting Organ-Level Lung Functions on a Chip"., Science (80-. ). 2010, 328 (5986), 1662-1668. https://doi.org/10.1126/science.1188302.
Li, M.; Qian, M.; Kyler, K.; Xu, J., "Endothelial-Vascular Smooth Muscle Cells Interactions in Atherosclerosis"., Front. Cardiovasc. Med. 2018, 5. https://doi.org/10.3389/fcvm.2018.00151.
Truskey, G. A., "Endothelial Vascular Smooth Muscle Cell Coculture Assay for High Throughput Screening Assays to Identify Antiangiogenic and Other Therapeutic Molecules",. Int. J. High Throughput Screen. 2010, 171. https://doi.org/10.2147/IJHTS.S13459.
Palchesko, R. N.; Zhang, L.; Sun, Y.; Feinberg, A. W., "Development of Polydimethylsiloxane Substrates with Tunable Elastic Modulus to Study Cell Mechanobiology in Muscle and Nerve",. PLoS One 2012, 7 (12). https://doi.org/10.1371/journal.pone.0051499.
Fischer, R. S.; Myers, K. A.; Gardel, M. L.; Waterman, C. M., "Stiffness-Controlled Three-Dimensional Extracellular Matrices for High-Resolution Imaging of Cell Behavior",. Nat. Protoc. 2012, 7 (11), 2056-2066. https://doi.org/10.1038/prot.2012.127.
Dardik, A.; Chen, L.; Frattini, J.; Asada, H.; Aziz, F.; Kudo, F. A.; Sumpio, B. E., "Differential Effects of Orbital and aminar Shear Stress on Endothelial Cells",. J. Vasc. Surg. 2005, 41 (5), 869-880. https://doi.org/10.1016/j.ivs.2005.01.020.
Denisin, A. K.; Pruitt, B. L., "Tuning the Range of Polyacrylamide Gel Stiffness for Mechanobiology Applications"., ACS Appl. Mater. Interfaces 2016, 8 (34), 21893-21902. https://doi.org/10.1021/acsami.5b09344.
Barnes, J. M.; Przybyla, L.; Weaver, V. M., "Tissue Mechanics Regulate Brain Development, Homeostasis and Disease",. J. Cell Sci. 2017, 130 (1), 71-82. https://doi.org/10.1242/jcs.191742.

(56) References Cited

OTHER PUBLICATIONS

Birukov, K. G.; Jacobson, J. R.; Flores, A. A.; Ye, S. Q.; Birukova, A. A.; Verin, A. D.; Garcia, J. G. N., "Magnitude- Dependent Regulation of Pulmonary Endothelial Cell Barrier Function by Cyclic Stretch",. Am. J. Physiol. Cell. Mol. Physiol. 2003, 285 (4), L785-L797. https://doi.org/10.1152/ajplung.00336.2002.

Engler, A. J.; Sen, S.; Sweeney, H. L.; Discher, D. E., "Matrix Elasticity Directs Stem Cell Lineage Specification"., Cell 2006, 126 (4), 677-689. https://doi.org/10.1016/j.cell.2006.06.044.

Wood, J. A.; Liliensiek, S. J.; Russell, P.; Nealey, P. F.; Murphy, C. J., "Biophysical Cueing and Vascular Endothelial Cell Behavior". Materials (Basel). 2010, 3 (3), 1620-1639. https://doi.org/10.3390/ma3031620.

Chien, S., "Mechanotransduction and Endothelial Cell Homeostasis: The Wisdom of the Cell",. Am. J. Physiol. Circ. Physiol. 2007, 292 (3), H1209-H1224. https://doi.org/10.1152/ajpheart.01047.2006.

Stojkovska, J.; Bugarski, B.; Obradovic, B., "Evaluation of Alginate Hydrogels under in Vivo-like Bioreactor Conditions for Cartilage Tissue Engineering", . J. Mater. Sci. Mater. Med. 2010, 21 (10), 2869-2879. https://doi.org/10.1007/s10856-010-4135-0.

Sugaya et al., "Elongation and Random orientation of Bovine Endothelial Cells in Response to Hydrostatic Pressue : Comparison with Response to Shear Stress", JSME International Journal Series C., vol. 46, No. 4, 2003. pp. 1248-1255.

Sinha, R.; Le Gac, S.; Verdonschot, N.; van den Berg, A.; Koopman, B.; Rouwkema, J., "Endothelial Cell Alignment as a Result of Anisotropic Strain and Flow Induced Shear Stress Combinations". Sci. Rep. 2016, 6 (1), 29510. https://doi.org/10.1038/srep29510.

Feng, S.; Mao, S.; Zhang, Q.; Li, W.; Lin, J.-M., "Online Analysis of Drug Toxicity to Cells with Shear Stress on an Integrated Microfluidic Chip",. ACS Sensors 2019, 4 (2), 521-527. https://doi.org/10.1021/acssensors.8b01696.

Mason, Brooke N et al. "Tuning three-dimensional collagen matrix stiffness independently of collagen concentration modulates endothelial cell behavior." Acta biomaterialia vol. 9,1 (2013): 4635-44. doi:10.1016/j.actbio.2012.08.007.

Yang, J.; Webb, A. R.; Pickerill, S. J.; Hageman, G.; Ameer, G. A. Synthesis and Evaluation of Poly(Diol Citrate) Biodegradable Elastomers. Biomaterials 2006, 27 (9), 1889-1898. https://doi.org/10.1016/j.biomaterials.2005.05.106.

Syed, S., etl., "Simple Polyacrylamide-Based Multiwell Stiffness Assay for the Study of Stiffness-Dependent Cell Responses",. J. Vis. Exp. 2015, No. 97. https://doi.org/10.3791/52643.

Simmons, Chelsey S et al. "Formation of composite polyacrylamide and silicone substrates for independent control of stiffness and strain." Lab on a chip vol. 13,4 (2013): 646-9. doi:10.1039/c2lc41110e.

Ramaswamy, Vidhya et al. "DNA Aptamer Assembly as a Vascular Endothelial Growth Factor Receptor Agonist." Nucleic acid therapeutics vol. 25,5 (2015): 227-34. doi: 10.1089/nat.2014.0519.

Ding, Yonghui et al. "High-Throughput Screening of Vascular Endothelium-Destructive or Protective Microenvironments: Cooperative Actions of Extracellular Matrix Composition, Stiffness, and Structure." Advanced healthcare materials vol. 6,11 (2017): 10.1002/adhm.201601426. doi:10.1002/adhm.201601426.

Davis, Caleb A et al. "Device-based in vitro techniques for mechanical stimulation of vascular cells: a review." Journal of biomechanical engineering vol. 137,4 (2015): 040801. doi: 10.1115/1.4029016.

Liliensiek, Sara J et al. "Characterization of endothelial basement membrane nanotopography in rhesus macaque as a guide for vessel tissue engineering." Tissue engineering. Part A vol. 15,9 (2009): 2643-51. doi: 10.1089/ten.lea.2008.0284.

Gillies, Allison R, and Richard L Lieber. "Structure and function of the skeletal muscle extracellular matrix." Muscle & herve vol. 44,3 (2011): 318-31. doi: 10.1002/mus.22094.

Waters, Christopher M et al. "Mechanobiology in lung epithelial cells: measurements, perturbations, and responses." Comprehensive Physiology vol. 2,1 (2012): 1-29. doi: 10.1002/cphy.c100090.

Günay, Kemal Arda et al. "PEG-Anthracene Hydrogels as an On-Demand Stiffening Matrix to Study Mechanobiology." Angewandte Chemie (International ed. in English) vol. 58,29 (2019): 9912-9916. doi:10.1002/anie.201901989.

Rosales, Adrianne M et al. "Hydrogels with Reversible Mechanics to Probe Dynamic Cell Microenvironments." Angewandte Chemie (International ed. in English) vol. 56,40 (2017): 12132-12136. doi:10.1002/anie.201705684.

Regehr, Keil J et al. "Biological implications of polydimethylsiloxane-based microfluidic cell culture." Lab on a chip vol. 9,15 (2009): 2132-9. doi:10.1039/b903043c.

Savoji, Houman et al. "Cardiovascular disease models: A game changing paradigm in drug discovery and screening." Biomaterials vol. 198 (2019): 3-26. doi: 10.1016/j.biomaterials.2018.09.036.

Stageflexer, https://www.flexcellint.com/product/stageflexer, Flexcell International Corporation.

Cell Stretching System—Strex Cell, Simulate Physiological Conditions Using Our Specialized Stretching Devices, https://strexcell.com/cell-stretching-system/, accessed Nov. 23, 2021.

Cell Stretching Bioreactors | Flexcell International, https://www.flexcellint.com, pp. 1-9, accessed Nov. 23, 2021.

* cited by examiner

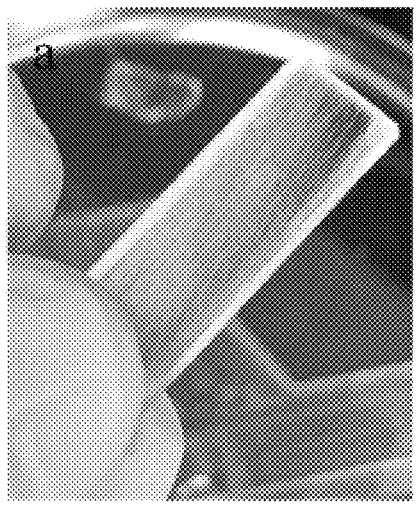
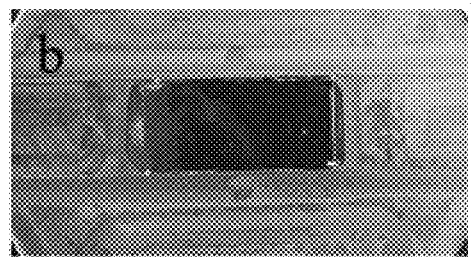
FIG. 17A   FIG. 17B
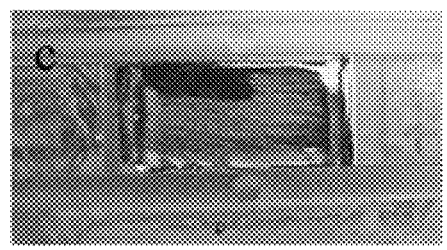
FIG. 17C   FIG. 17D

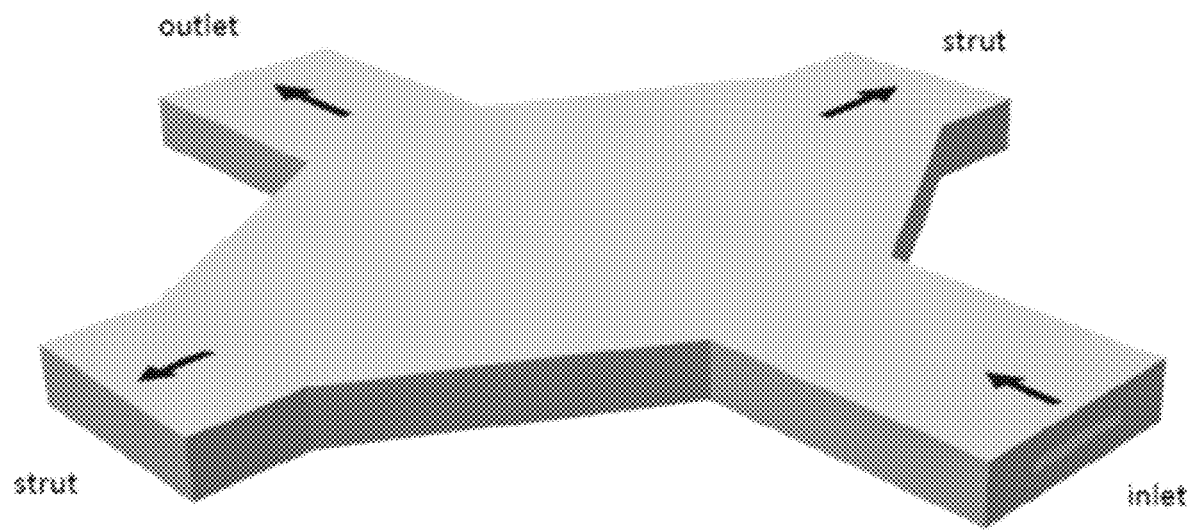
FIG. 19
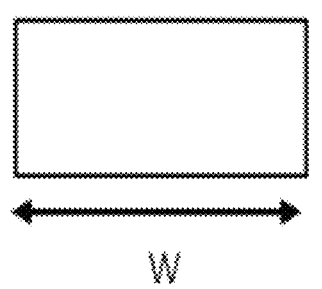
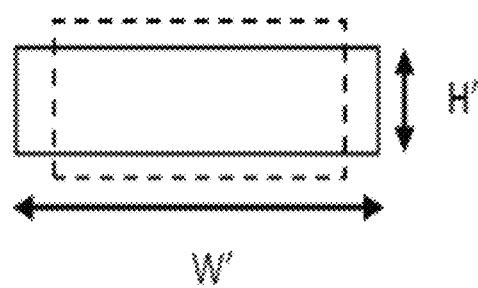
FIG. 20A  FIG. 20B

BIOREACTOR CHAMBER AND SYSTEMS THEREOF

CROSS-REFERENCE TO RELATED APPLICATIONS

This application is the 35 U.S.C. § 371 national stage entry of PCT Application No. PCT/US2020/013177, filed Jan. 10, 2020, where the PCT claims priority to, and the benefit of, U.S. provisional application entitled "BIOREACTOR CHAMBER AND SYSTEMS THEREOF" having Ser. No. 62/793,264, filed Jan. 16, 2019, both of which are incorporated herein by reference in their entireties.

BACKGROUND

Increasingly being recognized is the role of the complex microenvironment to regulate cell phenotype; however, the cell culture systems used to study these effects in vitro are lagging. The complex microenvironment is host to a combination of biological interactions, chemical factors, and mechanical stimuli. Many devices have been designed to probe the effects of one mechanical stimulus, but few are capable of systematically interrogating all combinations of mechanical stimuli with independent control. Accordingly, there is a need to address the aforementioned deficiencies and inadequacies.

SUMMARY

Described herein are bioreactor chambers, bioreactor systems, and methods of use. In embodiments, described herein are single-plate symmetrical bioreactor chambers. In certain aspects, a single-plate symmetrical bioreactor chamber comprises a flow channel extending along a first axis, wherein the flow channel comprises an inlet and an outlet at opposing ends of the flow channel; a pair of struts on opposing ends of a second axis, wherein the second axis is substantially perpendicular to the first axis, wherein each strut of the pair of struts are placed on opposing sides of the flow channel, wherein the struts are configured to be coupled to a bi-directional linear actuator and configured to provide a strain perpendicular to a fluid flow through the flow channel, wherein the strain does not laterally displace cells present in the flow channel.

In embodiments according to the present disclosure, at least a portion of the bioreactor chamber is composed of a stretchable material. In embodiments according to the present disclosure, at least a portion of the bioreactor chamber is composed of a silicone rubber. In embodiments according to the present disclosure, at least a portion of the bioreactor chamber is optically translucent. In embodiments according to the present disclosure, the bioreactor chamber is configured to generate a cyclical strain to the flow channel.

In embodiments, bioreactor chambers according to the present disclosure further comprise a cell growth substrate. In embodiments according to the present disclosure, the cell growth substrate is a portion of the bioreactor chamber. In embodiments according to the present disclosure, the cell growth substrate is stretchable. In embodiments according to the present disclosure, the cell growth substrate is a silicone material, silicone composite silicone substrate, a silicone rubber substrate, a citrate-based elastomer substrate, or hydrogel substrate, individually or in combination. In embodiments according to the present disclosure, the cell growth substrate is a silicone material, silicone composite. In embodiments according to the present disclosure, the bioreactor chamber comprises top and bottom halves, wherein the cell growth substrate is coupled between the top and bottom halves of the bioreactor chamber.

In embodiments, bioreactor chambers according to the present disclosure further comprise a cell growth matrix. In embodiments according to the present disclosure, the cell growth matrix is one or more of silicones, polyacrylamides, collagen gels, fibronectins, poly(diol citrates), alginates, polyethylene glycol hydrogels, polyhydroxyalkanoates, hyaluronic acid hydrogels, or polyacrylic acids, individually or in combination. In embodiments according to the present disclosure, the cell growth matrix is a biomolecule matrix. In embodiments according to the present disclosure, the biomolecule matrix comprises extracellular matrix proteins such as collagen, fibronectin, laminin or adhesion peptides such as RGD and YIGSR. In embodiments according to the present disclosure, the cell growth matrix comprises polydimethylsiloxane elastomer, polyacrylamide gel, poly(1,8-octanediol citrate) elastomer, type I collagen gel, or fibronectin, individually or in combination. In embodiments according to the present disclosure, the cell growth matrix is conjugated to the cell growth substrate. In embodiments according to the present disclosure, the cell growth matrix is conjugated to the cell growth substrate using sulfo-SANPAH photocrosslinking chemistry or NHS-EDC carbodiimide chemistry. In embodiments according to the present disclosure, the cell growth substrate comprises one or more of polydimethylsiloxane elastomer, polyacrylamide gel, poly(1,8-octanediol citrate) elastomer, and type I collagen gel.

Also described herein are bioreactor systems. In embodiments according to the present disclosure, bioreactor systems comprise a bioreactor chamber comprising a flow channel extending along a first axis, wherein the flow channel comprises an inlet and an outlet at opposing ends of the flow channel, and wherein the bioreactor chamber further comprises a pair of struts on opposing ends of a second axis, wherein the second axis is substantially perpendicular to the first axis, wherein each strut of the pair of struts are placed on opposing sides of the flow channel, wherein the struts are configured to be coupled to a bi-directional linear actuator and configured to provide a strain perpendicular to a fluid flow through the flow channel, wherein the strain does not laterally displace cells present in the flow channel; a fluid flow circuit, wherein the fluid flow circuit is fluidly coupled to the flow channel of the bioreactor chamber; a bi-directional linear actuator, wherein the bidirectional linear actuator is coupled to the pair of struts of the bioreactor chamber; and a control system, wherein the control system is physically coupled, electrically coupled, and/or otherwise in communication with the bioreactor chamber, the fluid flow circuit, and/or the linear actuator.

In embodiments according to the present disclosure, bioreactor systems as described herein further comprise a hydrostatic pressure linear actuator, wherein the hydrostatic pressure linear actuator is fluidly coupled to the fluid flow circuit and physically coupled, electrically coupled, and/or otherwise in communication with the control system.

In embodiments of bioreactor systems according to the present disclosure, at least a portion of the bioreactor chamber is composed of a stretchable material. In embodiments of bioreactor systems according to the present disclosure, at least a portion of the bioreactor chamber is composed of a silicone rubber. In embodiments of bioreactor systems according to the present disclosure, at least a portion of the bioreactor chamber is optically transparent.

In embodiments of bioreactor systems according to the present disclosure, the bioreactor chamber is configured to generate a cyclical strain to the flow channel.

In embodiments of bioreactor systems according to the present disclosure, the bioreactor chamber further comprises a cell growth substrate. In embodiments of bioreactor systems according to the present disclosure, the cell growth substrate is a portion of the bioreactor chamber.

In embodiments of bioreactor systems according to the present disclosure, the bioreactor chamber comprises top and bottom halves, wherein the cell growth substrate is coupled between the top and bottom halves of the bioreactor chamber. In embodiments of bioreactor systems according to the present disclosure, the cell growth substrate is stretchable. In embodiments of bioreactor systems according to the present disclosure, the cell growth substrate is a silicone material, silicone composite silicone substrate, a silicone rubber substrate, a citrate-based elastomer substrate, or hydrogel substrate, individually or in combination. In embodiments of bioreactor systems according to the present disclosure, the cell growth substrate is a silicone material, silicone composite.

In embodiments of bioreactor systems according to the present disclosure, the bioreactor chamber further comprises a cell growth matrix. In embodiments of bioreactor systems according to the present disclosure, the cell growth matrix is one or more of silicones, polyacrylamides, collagen gels, fibronectins, poly(diol citrates), alginates, polyethylene glycol hydrogels, polyhydroxyalkanoates, hyaluronic acid hydrogels, or polyacrylic acids, individually or in combination. In embodiments of bioreactor systems according to the present disclosure, the cell growth matrix is a biomolecule matrix. In embodiments of bioreactor systems according to the present disclosure, the biomolecule matrix comprises extracellular matrix proteins such as collagen, fibronectin, laminin or adhesion peptides such as RGD and YIGSR. In embodiments of bioreactor systems according to the present disclosure, the cell growth matrix comprises polydimethylsiloxane elastomer, polyacrylamide gel, poly(1,8-octanediol citrate) elastomer, type I collagen gel, or fibronectin, individually or in combination. In embodiments of bioreactor systems according to the present disclosure, the cell growth matrix is conjugated to the cell growth substrate. In embodiments of bioreactor systems according to the present disclosure, the cell growth matrix is conjugated to the cell growth substrate using sulfo-SANPAH photocrosslinking chemistry or NHS-EDC carbodiimide chemistry. In embodiments of bioreactor systems according to the present disclosure, the cell growth substrate comprises one or more of polydimethylsiloxane elastomer, polyacrylamide gel, poly (1,8-octanediol citrate) elastomer, and type I collagen gel.

Described herein are methods of operating a bioreactor system as described herein. In embodiments of methods according to the present disclosure, described herein is a method of operating the bioreactor system as described herein, comprising: immobilizing cells within the fluid flow channel of the bioreactor chamber; applying a fluid flow in a first direction along a first axis; simultaneously pulling both struts in opposite directions away from each other and in a direction along a second axis to apply a strain to the immobilized cells, wherein the second axis is substantially perpendicular to the first axis, wherein the cells are not laterally displaced along the second axis.

In embodiments of methods according to the present disclosure, the linear actuator simultaneously pulls both struts.

In embodiments of methods according to the present disclosure, the cells are immobilized on the cell growth substrate.

In embodiments of methods according to the present disclosure, the cells are immobilized in a cell growth matrix, wherein the cell growth matrix is attached coupled to the cell growth substrate.

In embodiments of methods according to the present disclosure, the cell growth matrix comprises polydimethylsiloxane elastomer, polyacrylamide gel, poly(1,8-octanediol citrate) elastomer, type I collagen gel, or fibronectin, individually or in combination.

In embodiments of methods according to the present disclosure, the cell growth matrix is applied at discrete locations on the cell growth substrate.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

Figure 4A:
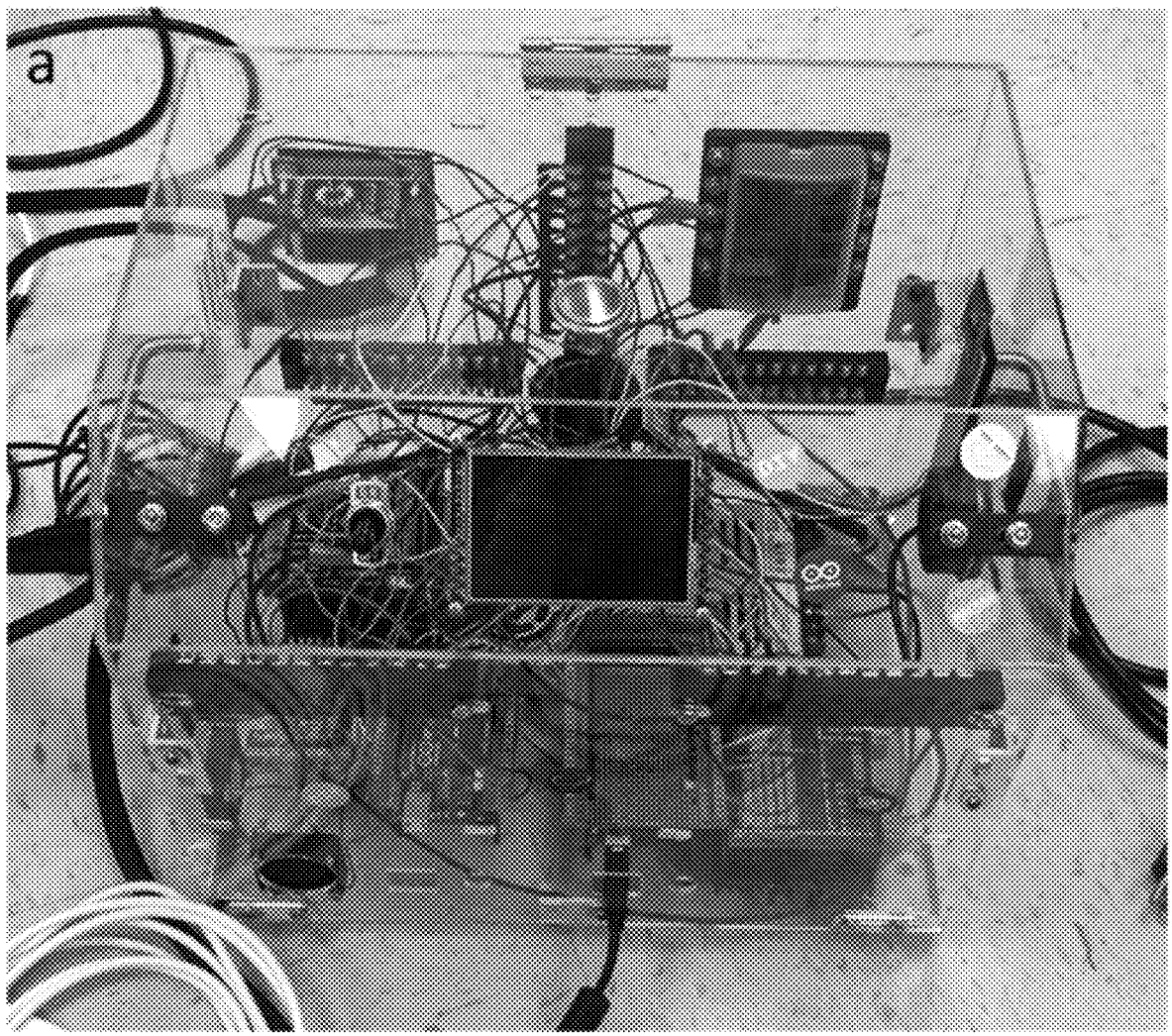
FIGS. 4A-4B are a photograph of a reduced-to-practice embodiment of the MechanoBioTester control box and a circuit diagram of the same. The control box is an external peripheral comprising open-source electronics (FIG. 4A).
Figure 4B:
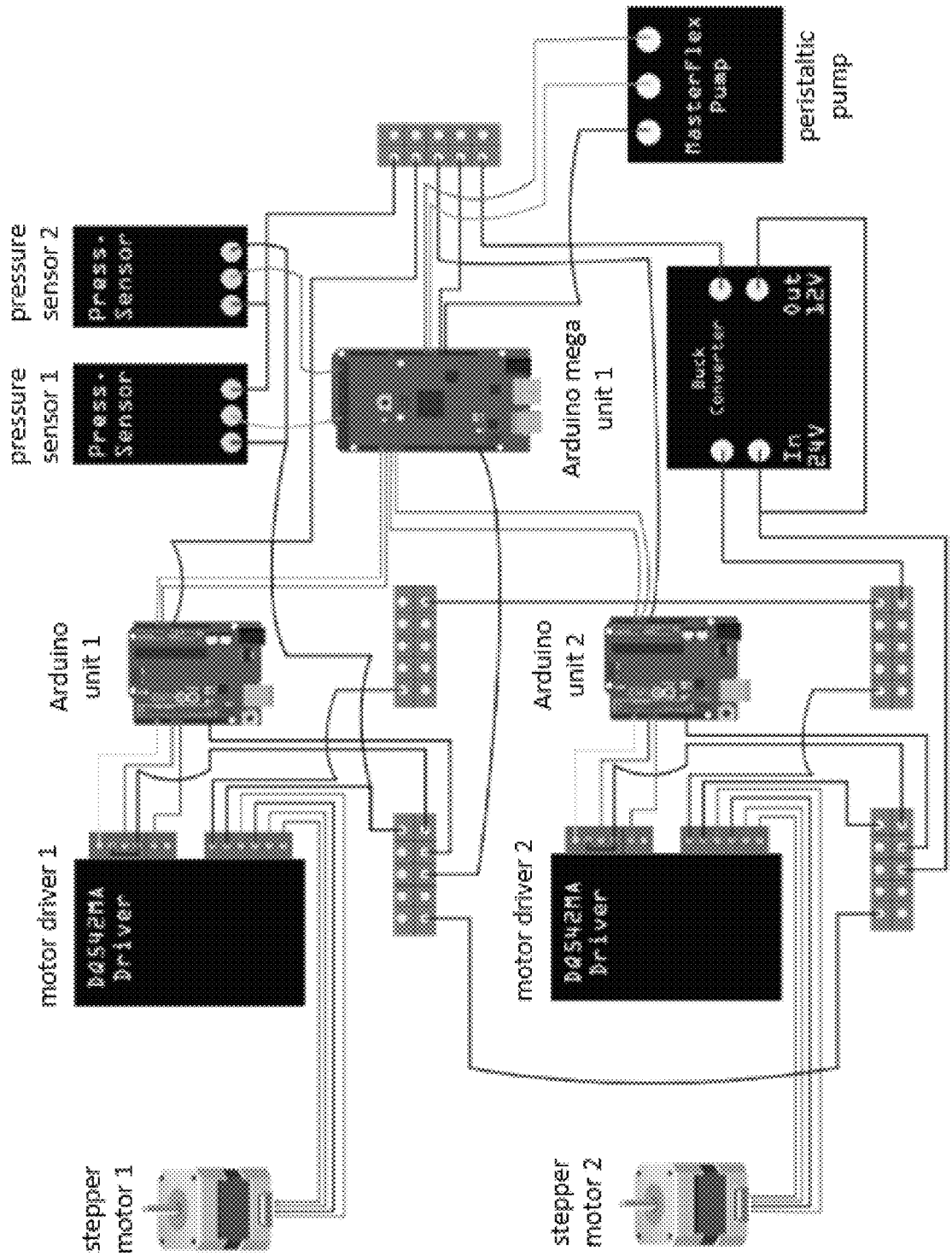

The system can use a series of 3 Arduino microcontrollers to coordinate the peristaltic pump, linear actuators, and sensors (FIG. 4B).

Figure 5A:
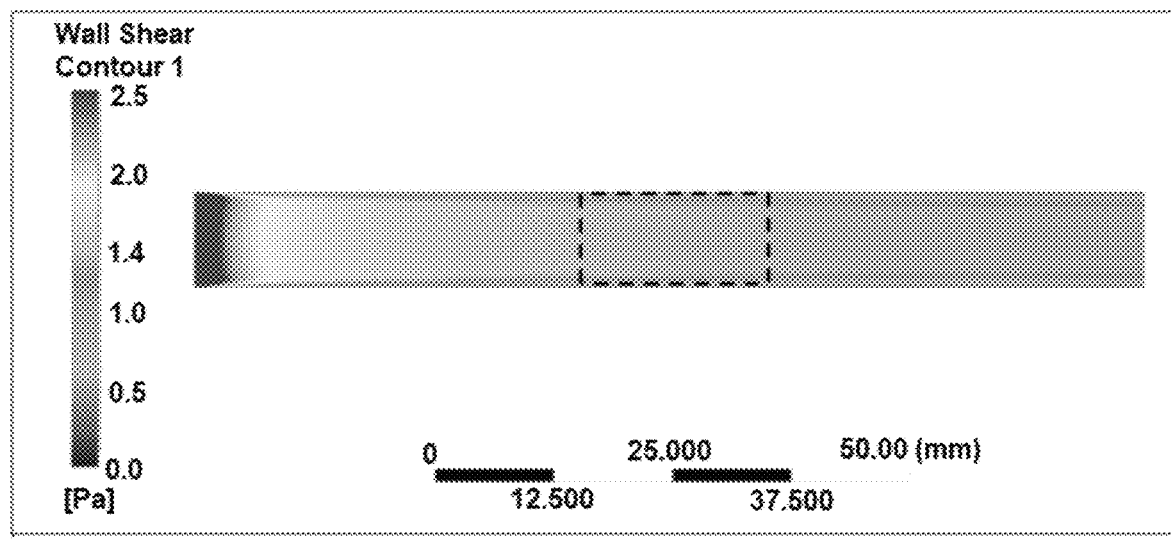
Figure 5B:
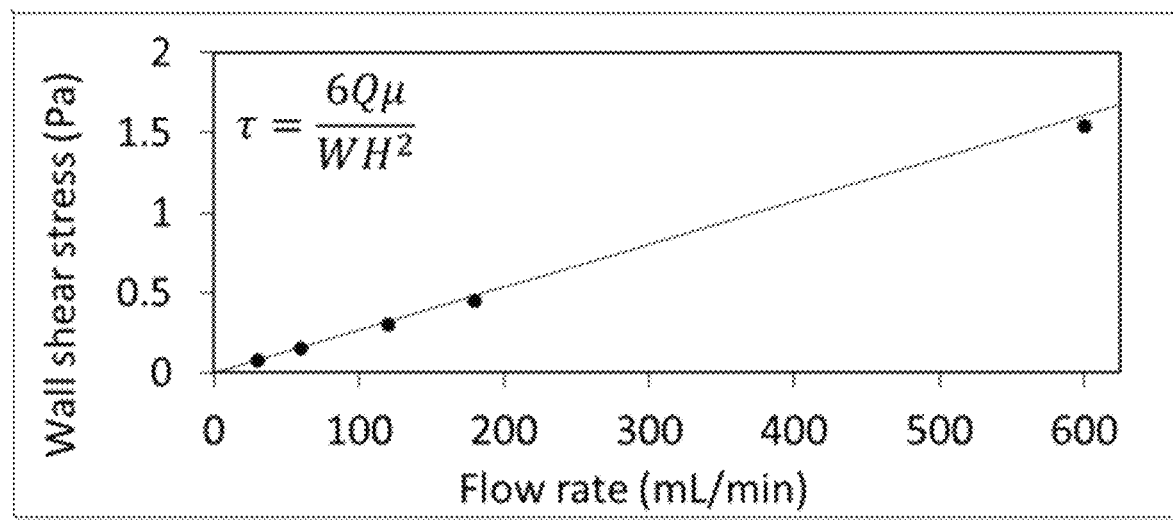

FIGS. 5A-5B are data plots representing wall shear stress and flow through the chamber. Example profile of the wall shear stress in the flow channel, with the location of the CCR, indicated by the dashed rectangle, for a flow rate of 600 mL/min (FIG. 5A). Wall shear stress varied linearly with flow rate in agreement with the solution of the Navier-Stokes equation for a parallel-plate flow chamber, shown as an inset where $\tau$ is the wall shear stress, Q is the volumetric flow rate, $\mu$ is the fluid dynamic viscosity, W is the channel width, and H is the channel height (FIG. 5B).

Figure 6:
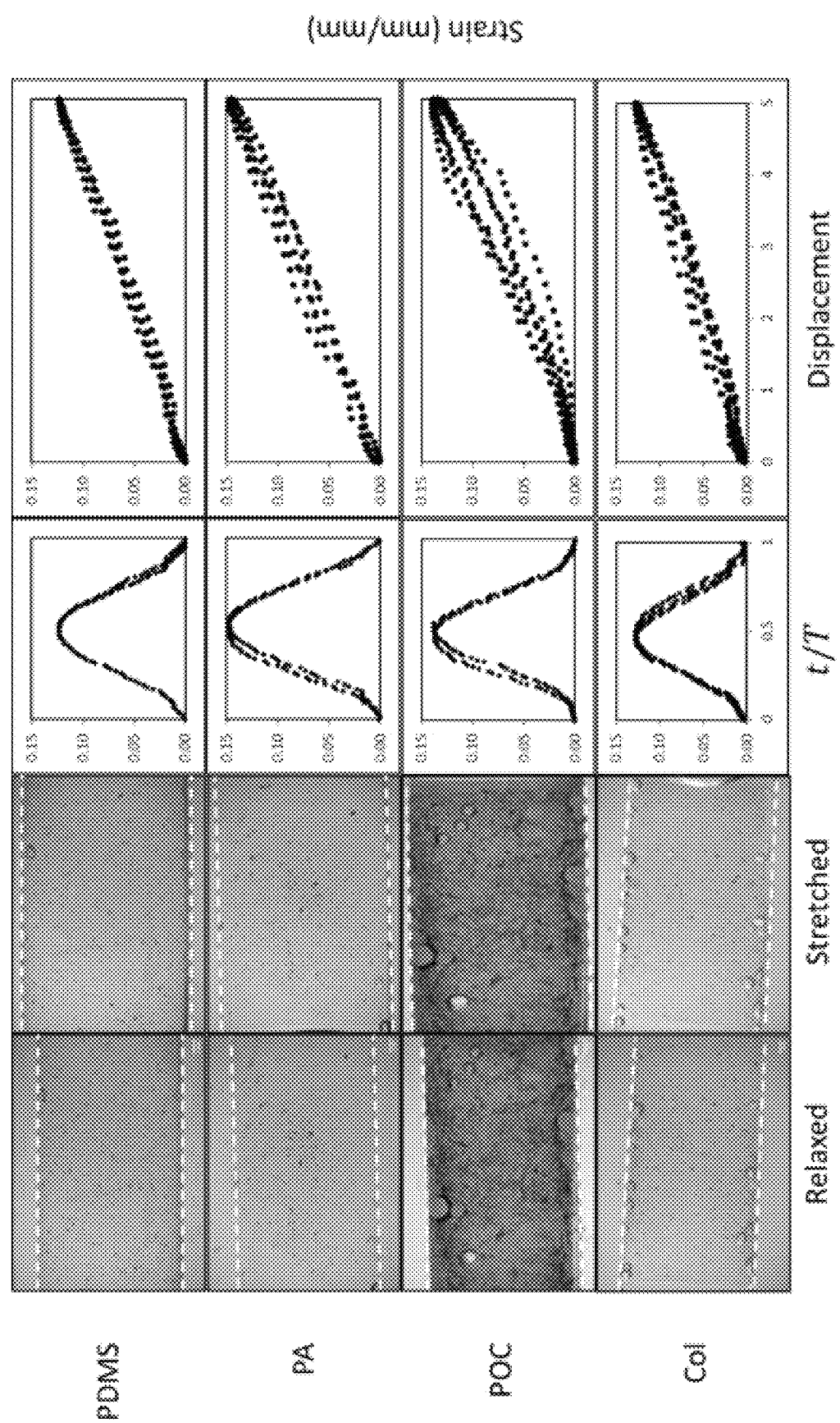

FIG. 6 shows photographs and data plots illustrating strain transfer to the CCR. The first two columns on the left show images of the tested material substrates: polydimethylsiloxane (PDMS), polyacrylamide (PA), poly(1,8-octanediol citrate) elastomer (POC) and type I collagen gel (Col) impregnated with charcoal powder, before (relaxed) and after being stretched. The third column shows a cyclic strain profile achieved using the microcontroller directed chamber stretcher. The profiles for each material were consistent over multiple periods (T). The fourth panel shows the linear relationship between strut displacement and CCR average equivalent strain for each material. The average equivalent strain varied slightly with each CCR filler material at larger displacements.

Figures 7A, 7B:
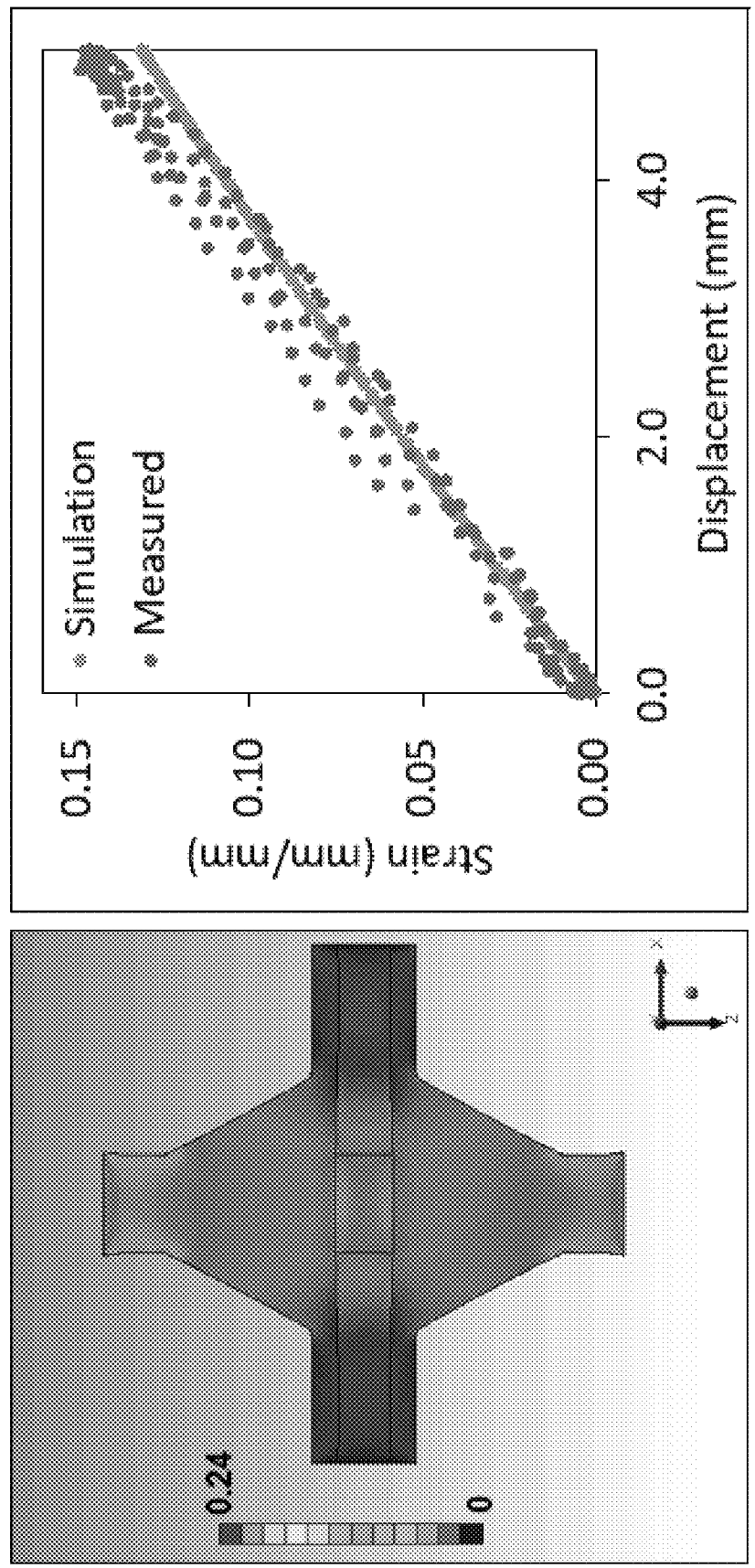

FIGS. 7A-7B are plots of ANSYS simulations of chamber stretching. The strain field of the CCR is near-uniform at 5 mm of strut displacement (FIG. 5A). The simulation results agreed with those measured by digital image correlation particle tracking (FIG. 5B). This simulation data is for a stretched polyacrylamide gel filled CCR with a modulus of 100 kPa.

Figures 8A, 8B:
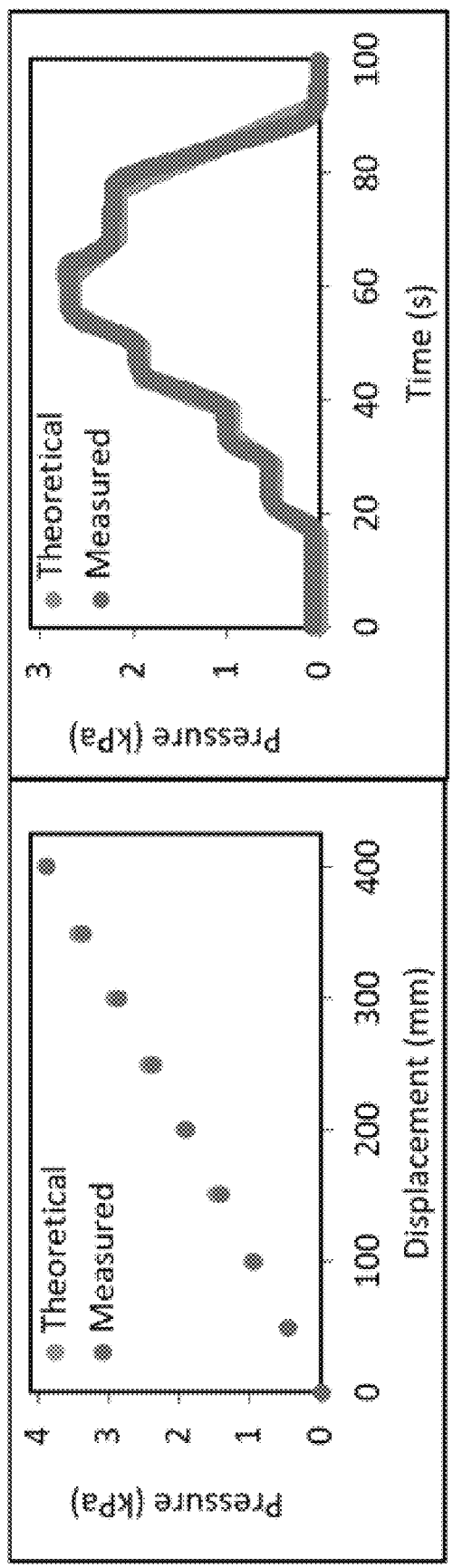

FIGS. 8A-8B show plots of controlled hydrostatic pressure. The hydrostatic pressure in the chamber changes linearly with vertical displacement of the media reservoir with respect to the chamber (FIG. 8A). The hydrostatic pressure responds to time-varying changes in vertical displacement (FIG. 8B). Measurements were made in triplicate.

Figures 9A, 9B:
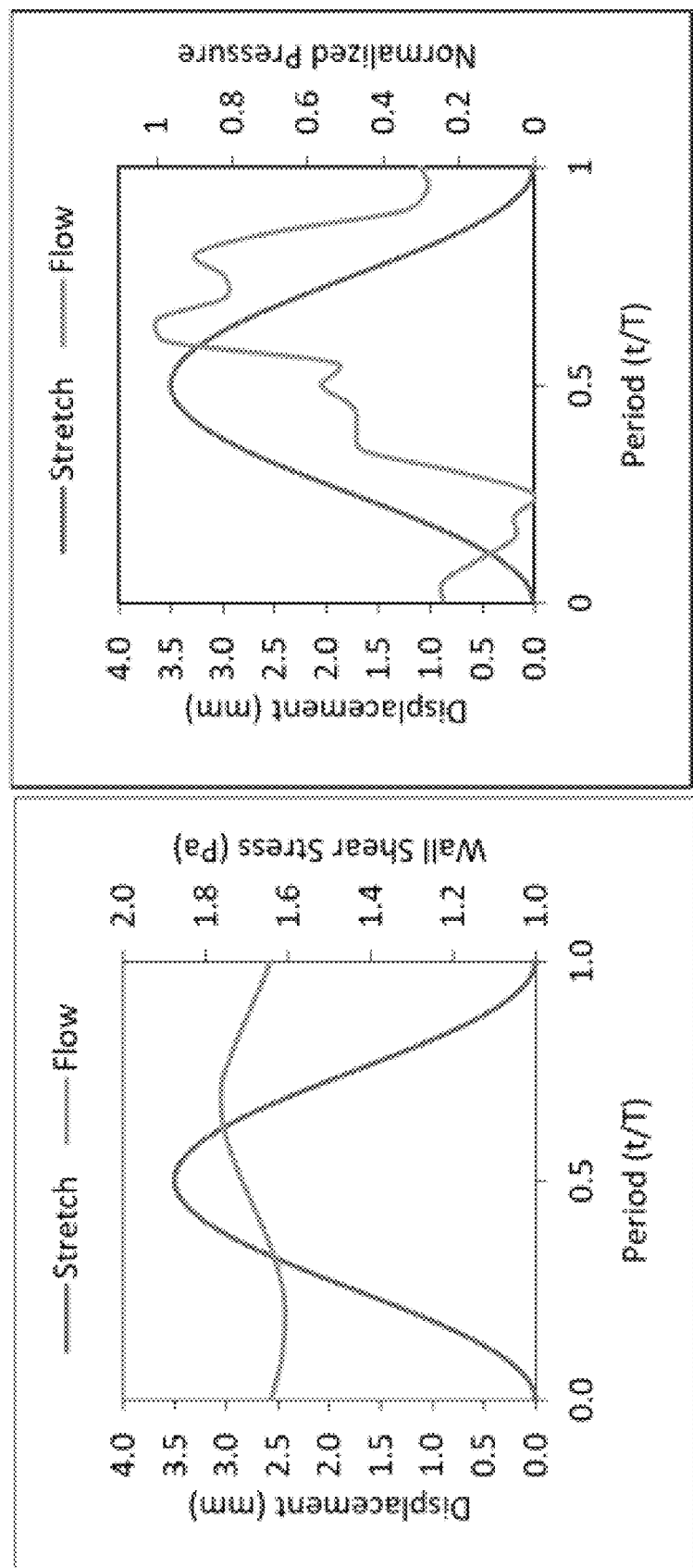

FIGS. 9A-9B are graphs of FSI simulation results. The simulation used a squared sinusoidal function to displace the struts 3.5 mm at a frequency of 1 Hz and a constant inlet flow rate of 600 mL/min (FIG. 9A). Cyclically stretching the chamber resulted in a sinusoidal-esque response in the WSS at the center of the CCR. The effect of stretching the chamber was observed by the in-line PendoTech pressure transducer due to the pumping action from stretching the chamber, which mirrors the simulated variation in the wall shear stress (FIG. 9B). A change in the dynamic pressure results in a change in the local flow rate through the chamber, which would lead to a variation in the wall shear stress (WSS) in the chamber.

Figures 10A, 10B:
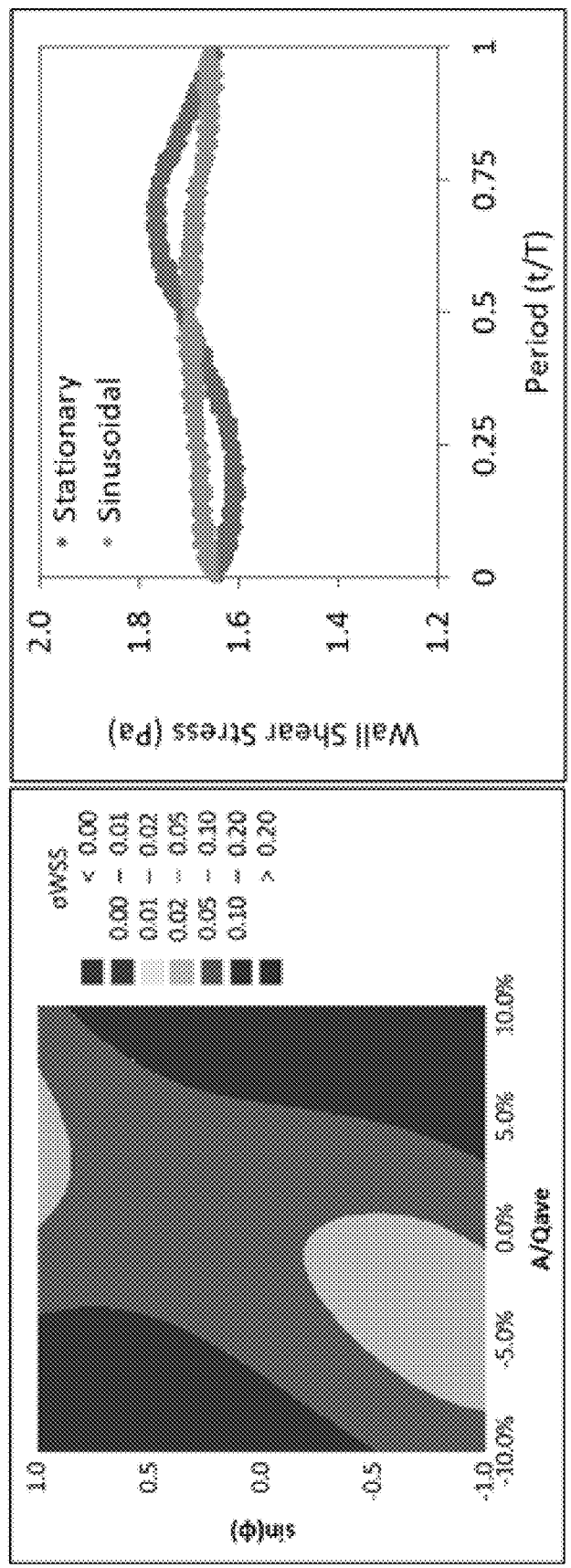

FIGS. 10A-10B: The standard deviation of the wall shear stress ($\sigma_{WSS}$) was minimized using a inlet flow rate with a generalized sine wave of the form, $Q_{in}=Q_{ave}-A\sin(\omega t-\phi)$. A transformed full $3^{rd}$ order regression model was used to fit the simulation data with an $R^2=96\%$ (FIG. 10A). The impact of the optimized parameters is clear from the plot of the WSS over the center of the CCR during one period (FIG. 10B). It was found for a given displacement that the variability of the WSS at the center of the CCR was minimized by a phase angle of ~90° and a ratio of $$\frac{A}{Q_{ave}}$$

of ~4 for a waveform of this type and a cyclic stretching amplitude of 3.5 mm of strut displacement.

Figure 11A:
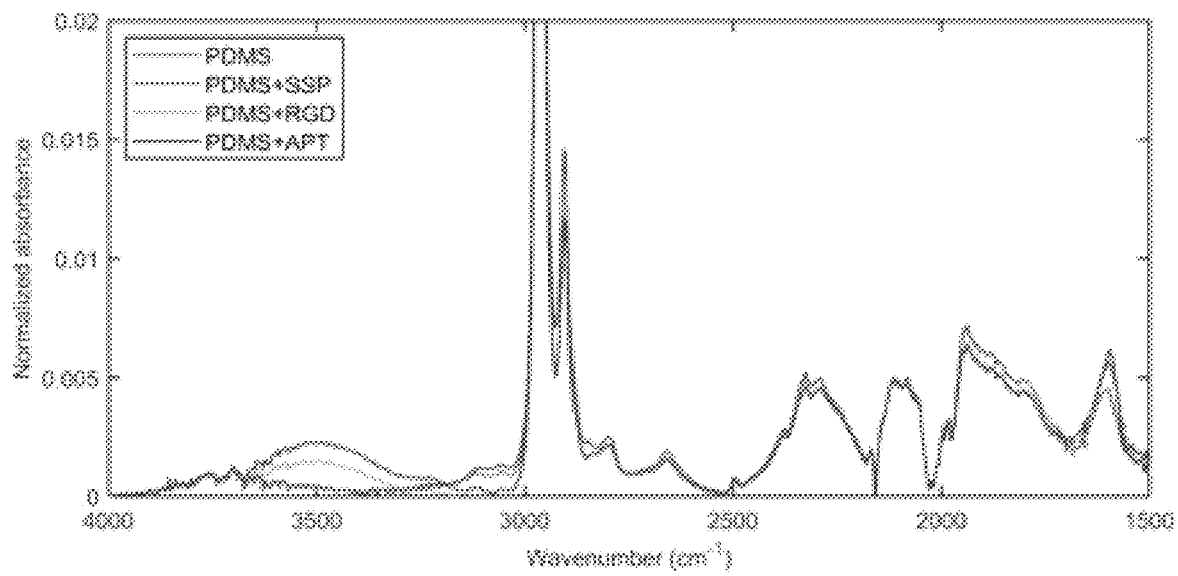
Figure 11B:
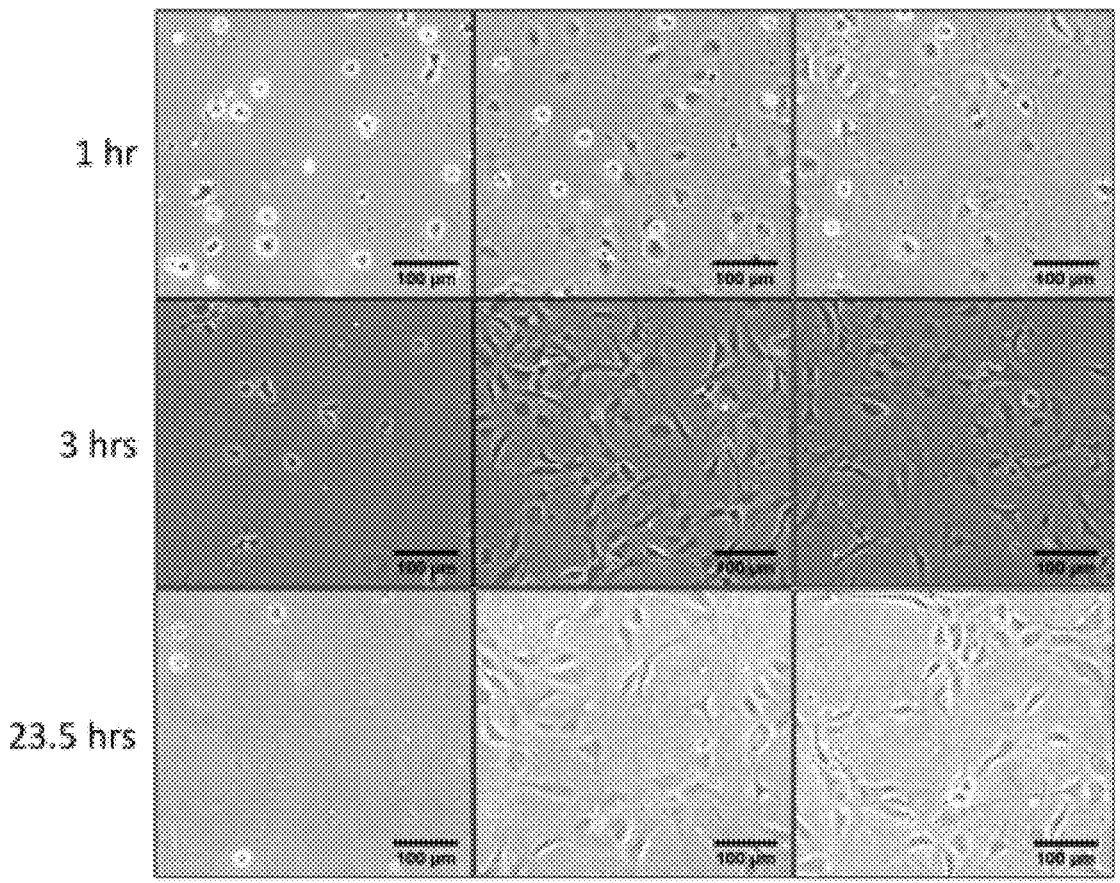

FIGS. 11A-11B shows biomolecule and cellular adhesion to the CCR of embodiments of systems as described herein. Conjugated protein, peptide, and DNA aptamer to a PDMS CCR using sulfo-SANPAH (SSP). The adhesion peptide sequence arginine-glycine-aspartate (RGD) and a DNA aptamer with a 5' amine functionality were the conjugation species. Their successful conjugation was seen in ATR-FTIR absorbance spectra by the presence of a broad peak at 3500 $cm^{-1}$ corresponding to the stretching of a N—H bond (FIG. 11A). This peak was absent from the PDMS substrate because PDMS does not have nitrogen atoms. The bottom panel of phase contrast images show the attachment of human umbilical vein endothelial cells on the different surface functionalities after over ~24 hours of incubation (FIG. 11B). As expected, the cells readily attached and spread to the treated surfaces, but not to the untreated PDMS.

Figures 12A, 12B:
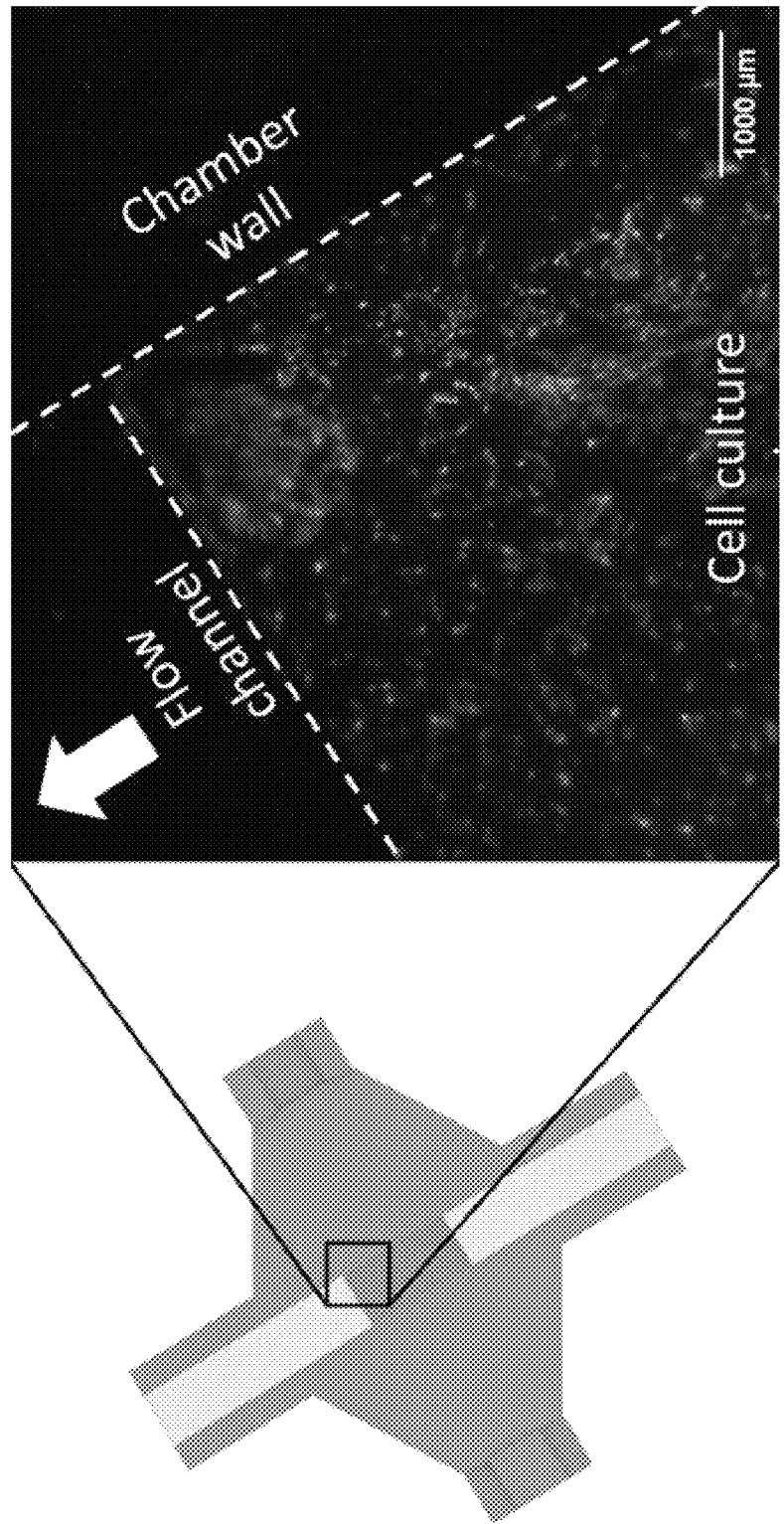

FIGS. 12A-12B is a photomicrograph of a region of a cell-seeded embodiment of a bioreactor as described herein. GFP-HUVECs (FIG. 12B) remained segregated to the cell culture region (CCR; FIG. 12A). GFP-HUVECs were seeded onto a type I collagen gel filled CCR. Cells remained confined to the CCR after seeding observed by the sharp interface between the corner of the CCR, the flow channel, and the chamber wall (dotted line). The image was taken using a DinoLite USB microscope with 480/510 nm and 570/610 nm excitation/emission capabilities.

Figure 13A:
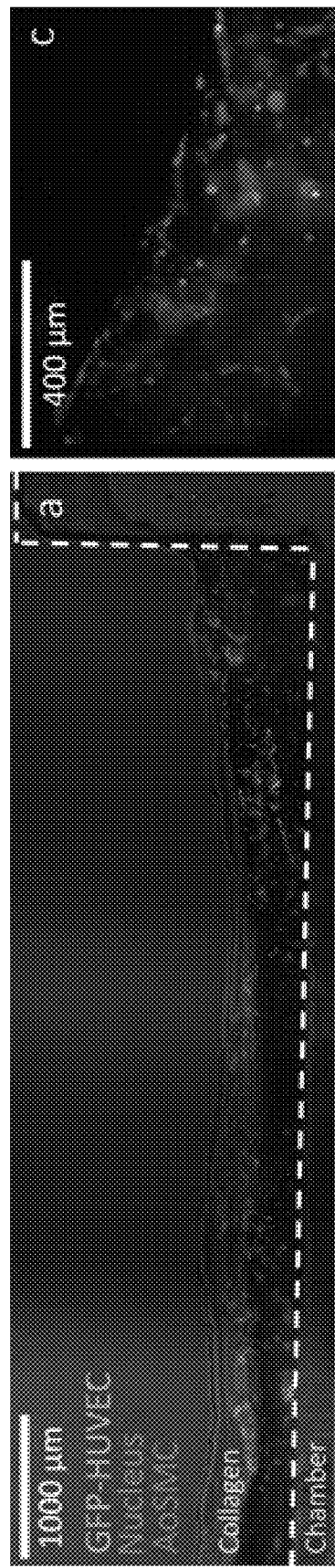
Figure 13B:
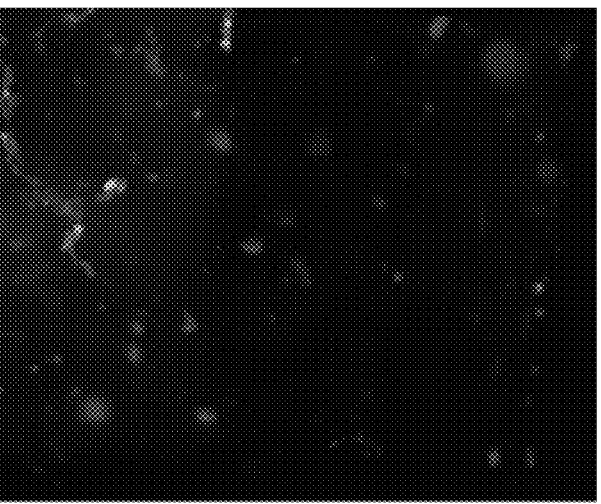
Figure 13C:
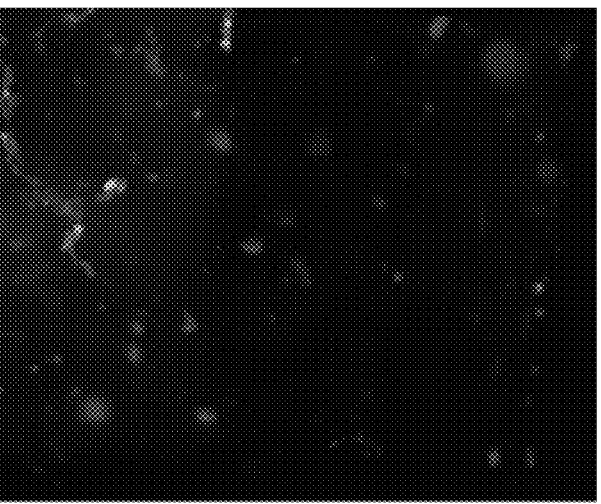

FIGS. 13A-13C are photomicrographs of embodiments of bioreactors according to the present disclosure and cell growth therein. A full thickness cross-section of the 3D co-culture model contained in the CCR of the chamber (FIG. 13A). A higher magnification view of GFP-HUVEC-AoSMC interface in the collagen gel (FIG. 13B). A full thickness image of the GFP-HUVEC-AoSMC 3D vascular co-culture model showed endothelial cell infiltration and organization after 3 days of co-culture (FIG. 13C).

Figure 14:
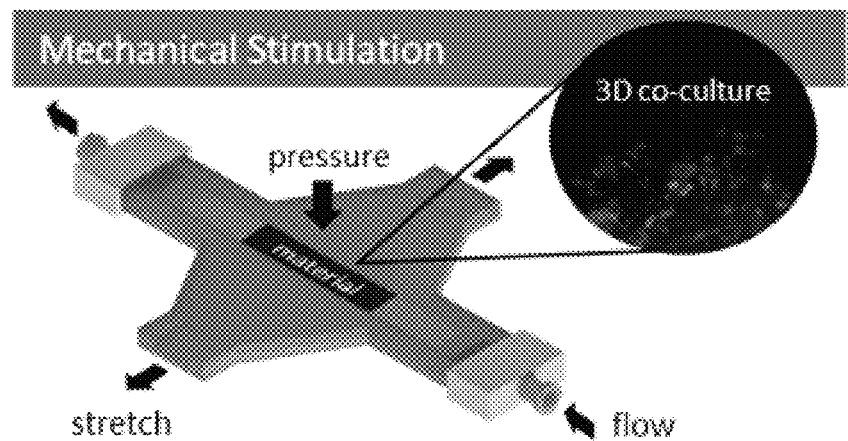

FIG. 14 is render with a photomicrograph inset of an embodiment of a method of using bioreactors according to the present disclosure.

Figures 15A, 15B:
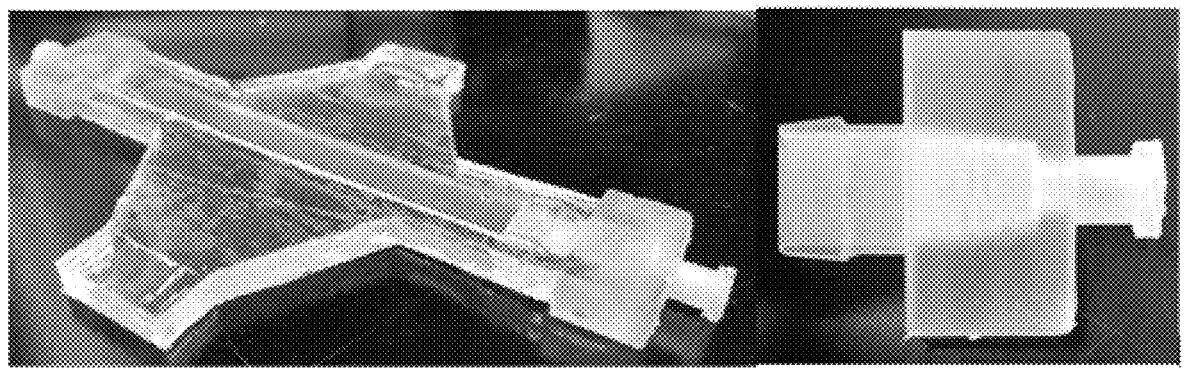

FIGS. 15A-15B are photographs of reduced-to-practice embodiments of the present disclosure. Custom luer lock fittings affixed to both the inlet and outlet of the bioreactor chamber (FIG. 15A). Top-view of the custom fitting showing the barbed end on the left and the male luer lock connection on the right (FIG. 15B). The parts were 3D printed in medical grade dental SG resin using a Form 2 stereolithographic 3D printed.

Figure 16:
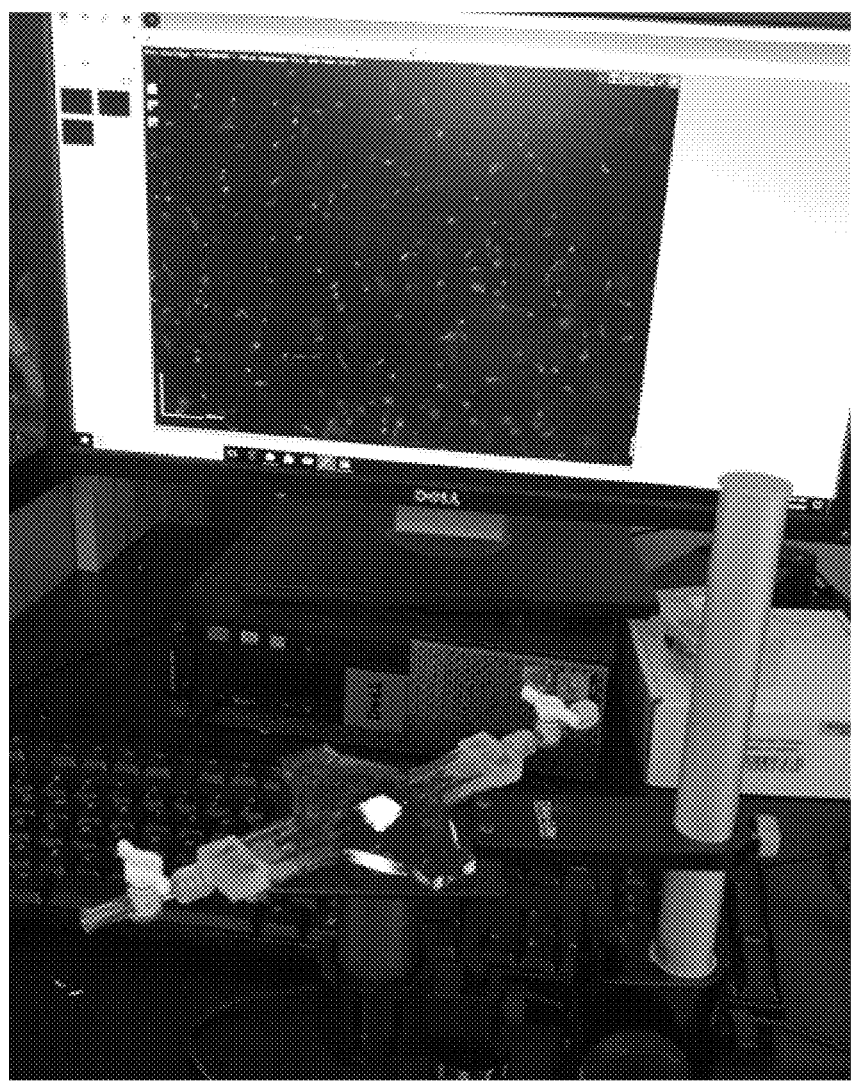

FIG. 16 is a photograph of a reduced-to-practice embodiment of the present disclosure of live cell imagine using bioreactors and methods as described herein. A DinoLite USB Fluorescence Microscope is used for live-cell imaging of green or red fluorescently-labeled cells in the chamber during culture.

FIGS. 17A-17D are photographs of reduced-to-practice aspects of the present disclosure, specifically relating to transfer of topography to CCR material. Utilizing both smooth and abraded Plexiglas coverslips (FIG. 17A), the PA filled chamber was polymerized with a smooth (FIG. 17B) or a rough surface topography (FIG. 17C). The transferred topography is also indicated by the increased opacity of the PA filled CCR. The Plexiglas coverslips are 30 mm in length to extend beyond the length of the CCR to prevent them from sinking into the uncured material (FIG. 17D).

Figure 18:
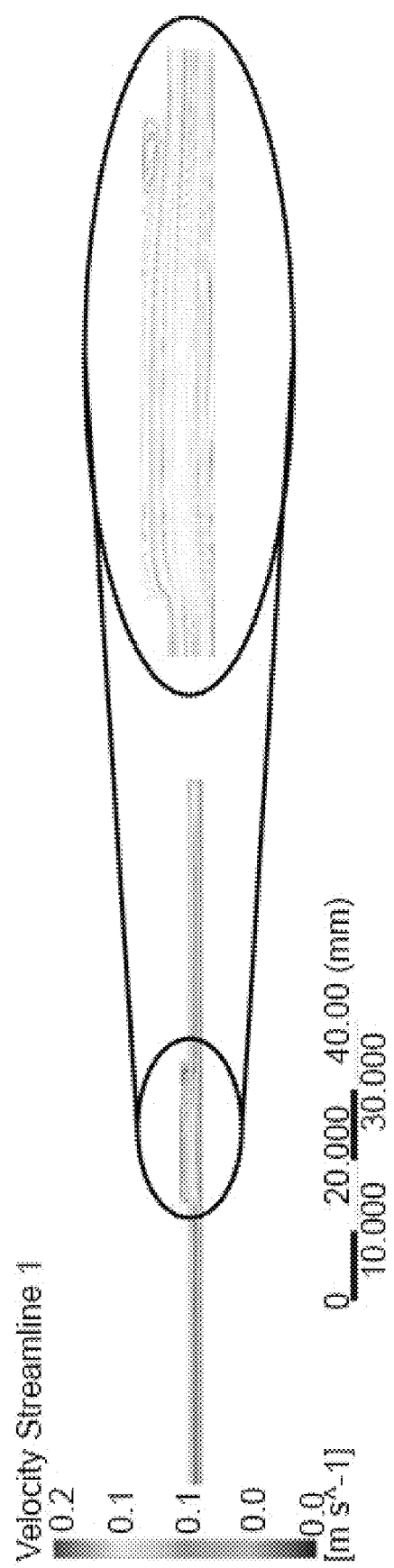

FIG. 18 shows simulation results of recirculating streamlines. Recirculating streamlines are present when there is a change in height within the flow channel as a result of the cell culture region being partially filled. This expands the capabilities of the chamber to be used for investigations concerning recirculating flow conditions.

FIG. 19 shows an embodiment of a bioreactor chamber as described herein.

FIGS. 20A-20B shows a cross section of a bioreactor chamber and the effective dimension changes of the cross section of the bioreactor chamber as a bi-lateral stretch/strain is applied to the base or other support structure upon which cells may be grown.

Figure 21:
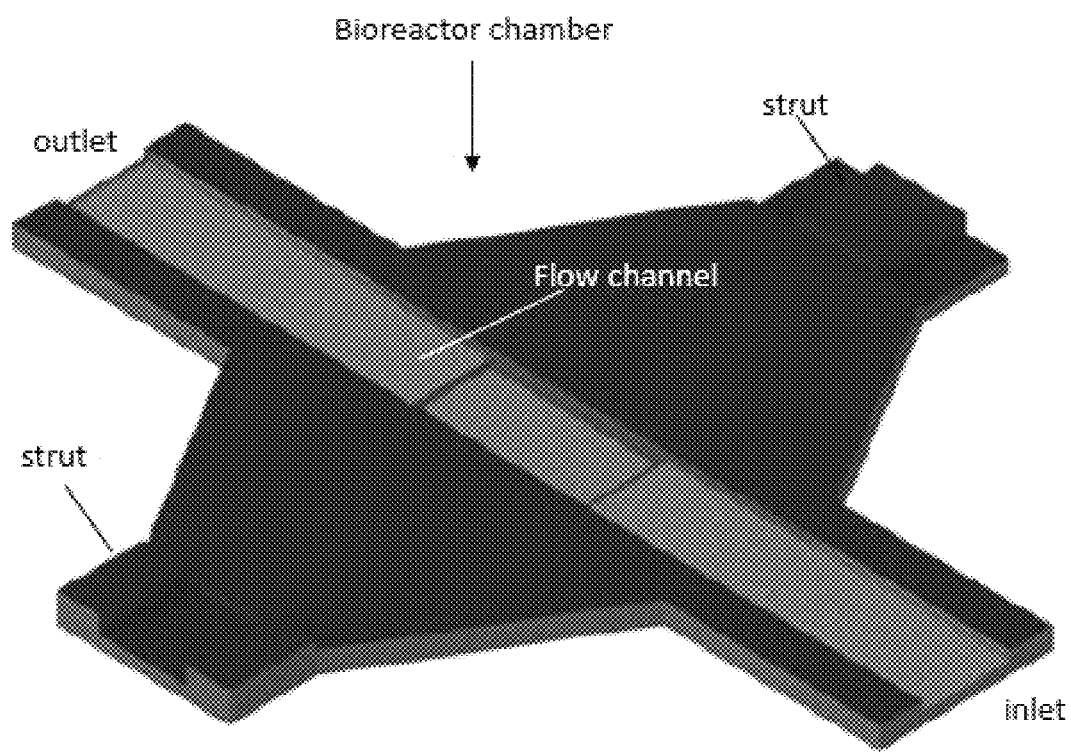

FIG. 21 shows a perspective view of the bioreactor chamber with the top half not shown.

Figure 22:
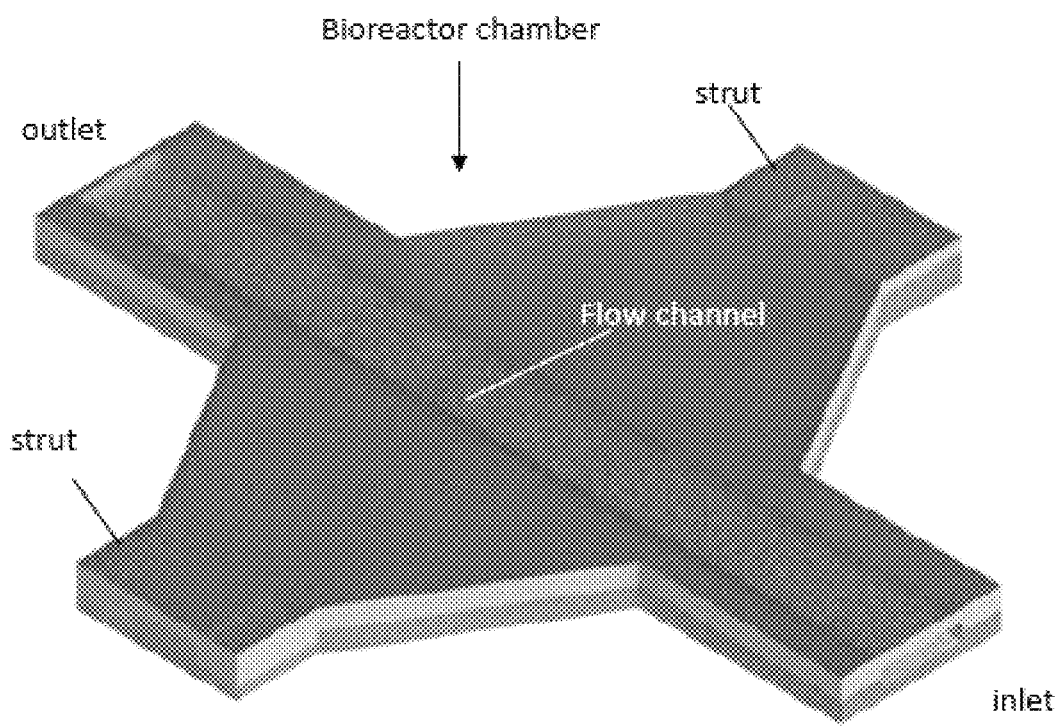

FIG. 22 shows a perspective view of the bioreactor chamber.

Figure 23:
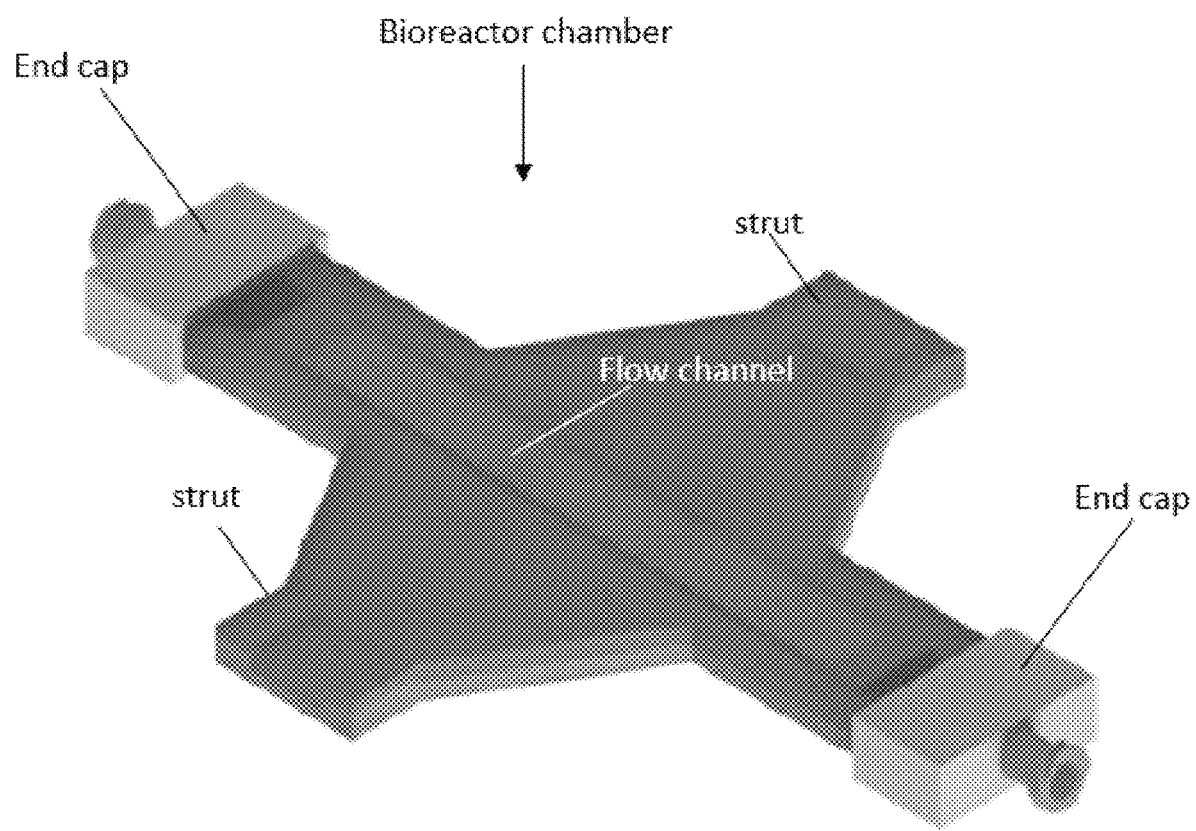
Figure 24A:
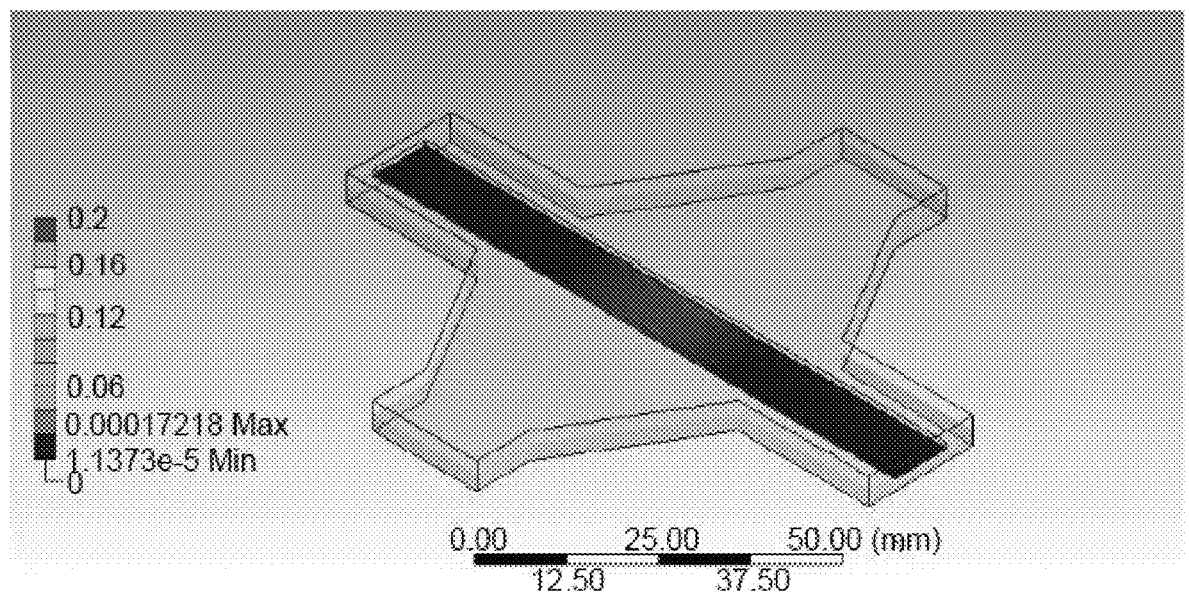
Figure 24B:
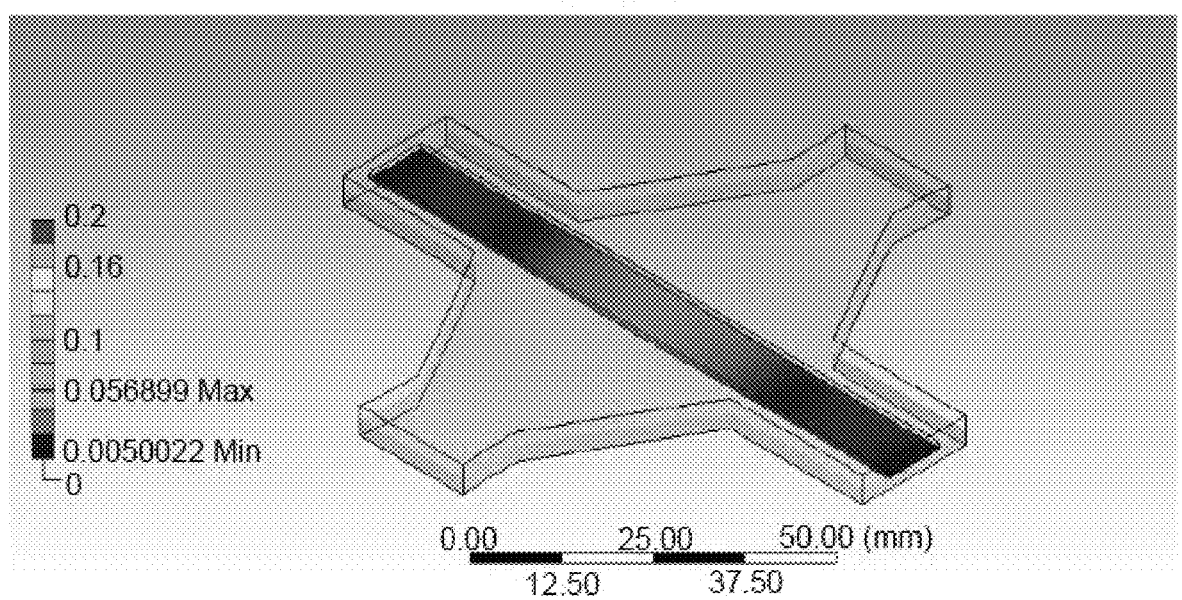
Figure 24C:
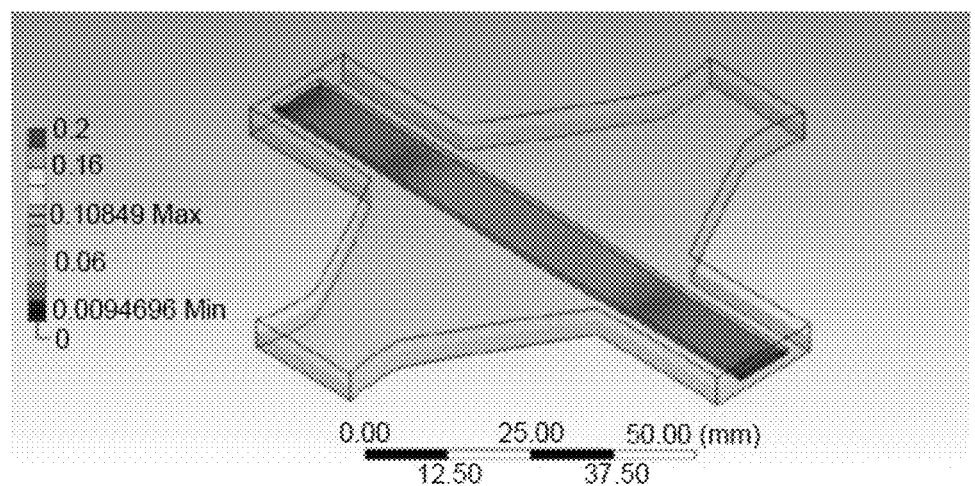
Figure 24D:
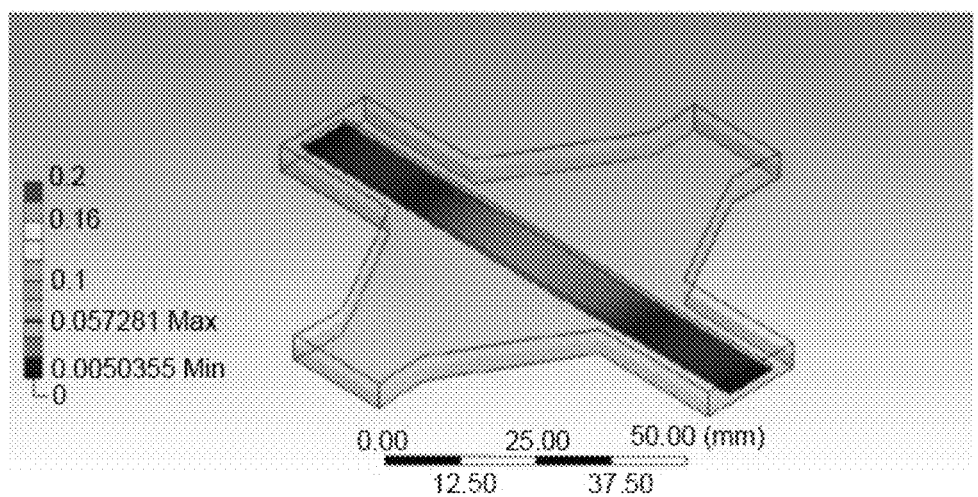
Figure 24E:
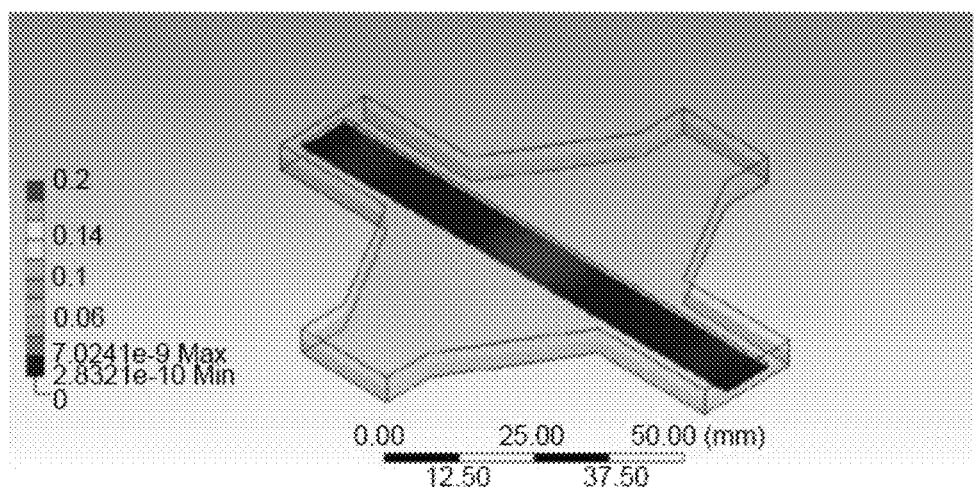

FIG. 23 shows a perspective view of the bioreactor chamber with end caps in place.

FIGS. 24A-24E show panel of contour plots of the total strain experienced by the bottom interior face of the flow channel (FIG. 24A) is at 0 s, (FIG. 24B) is at 0.25 s, (FIG. 24C) is at 0.50 s, (FIG. 24D) is at 0.75 s, and (FIG. 24E) is at 1.00 s.

Figure 25:
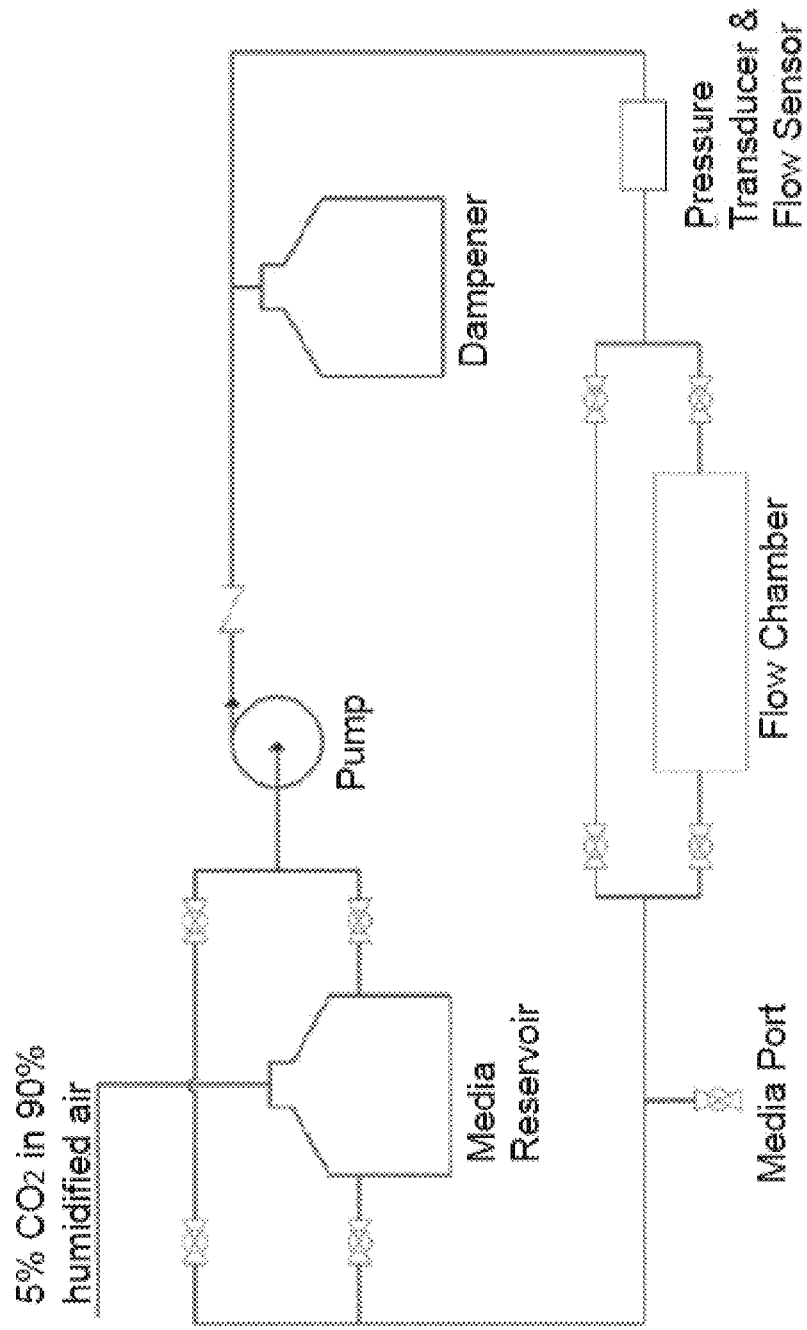

FIG. 25 is a diagram that can shows an embodiment of a flow circuit.

Figure 26:
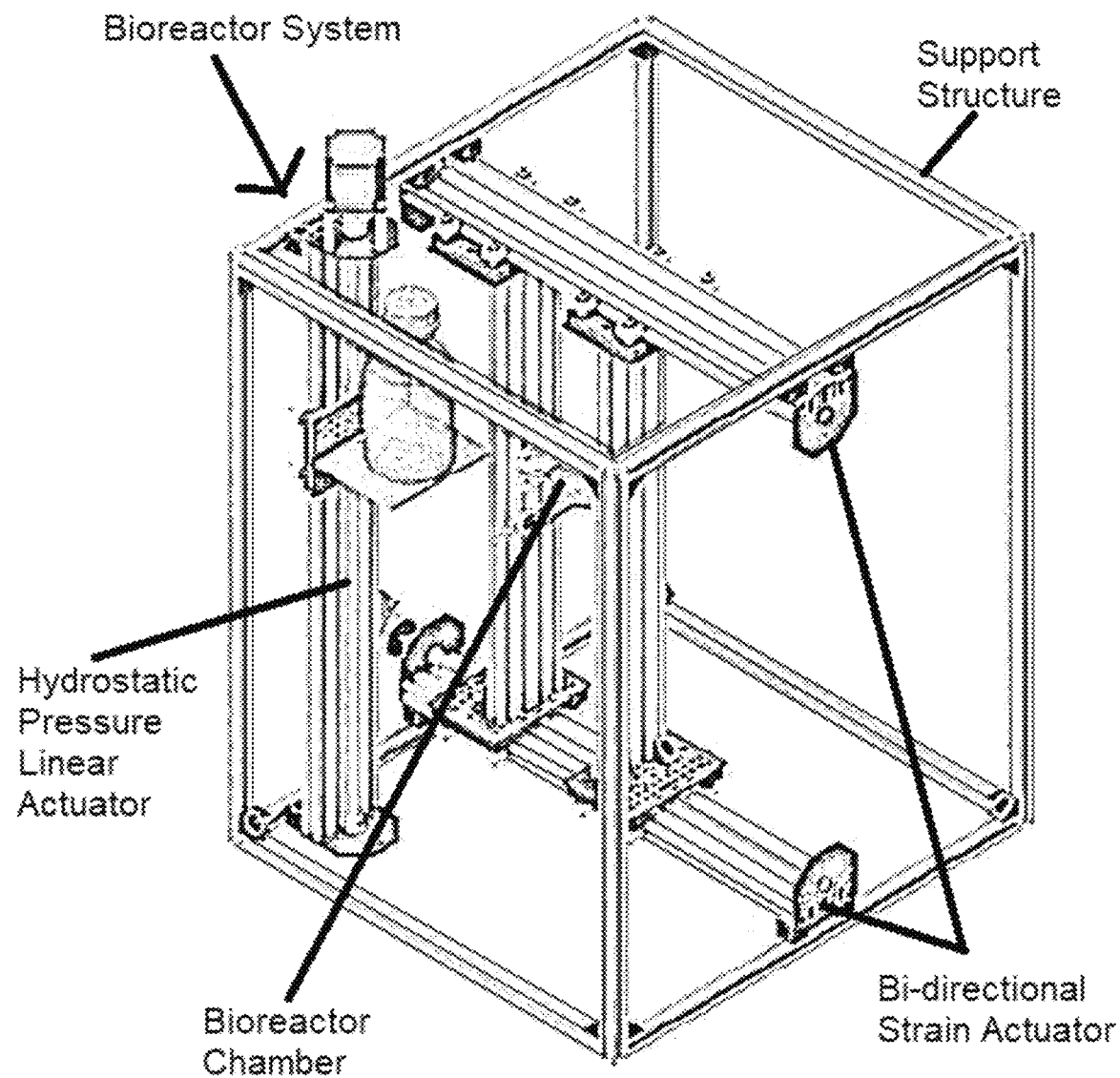

FIG. 26 shows one embodiment of a bioreactor system as described herein.

Figure 27:
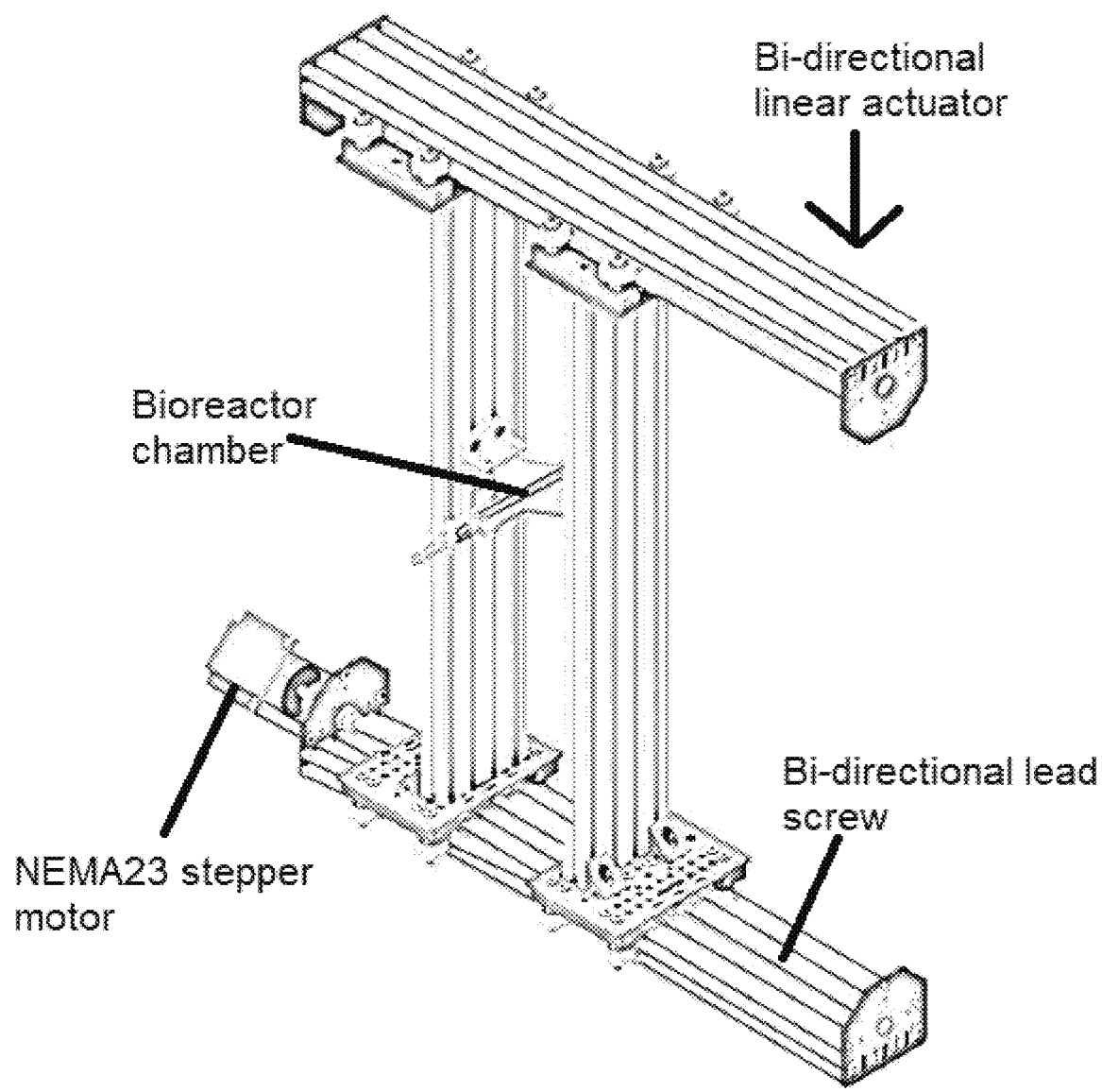

FIG. 27 shows one embodiment of a bi-directional strain actuator as described herein.

Figure 28:
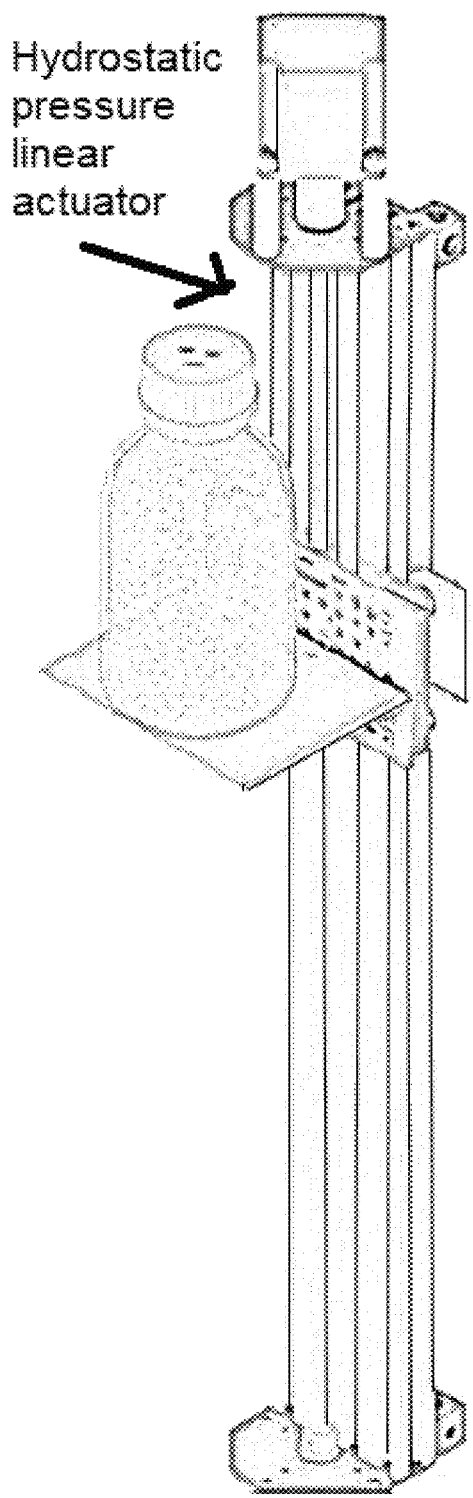

FIG. 28 shows one embodiment of a hydrostatic pressure linear actuator as described herein.

Figure 29:
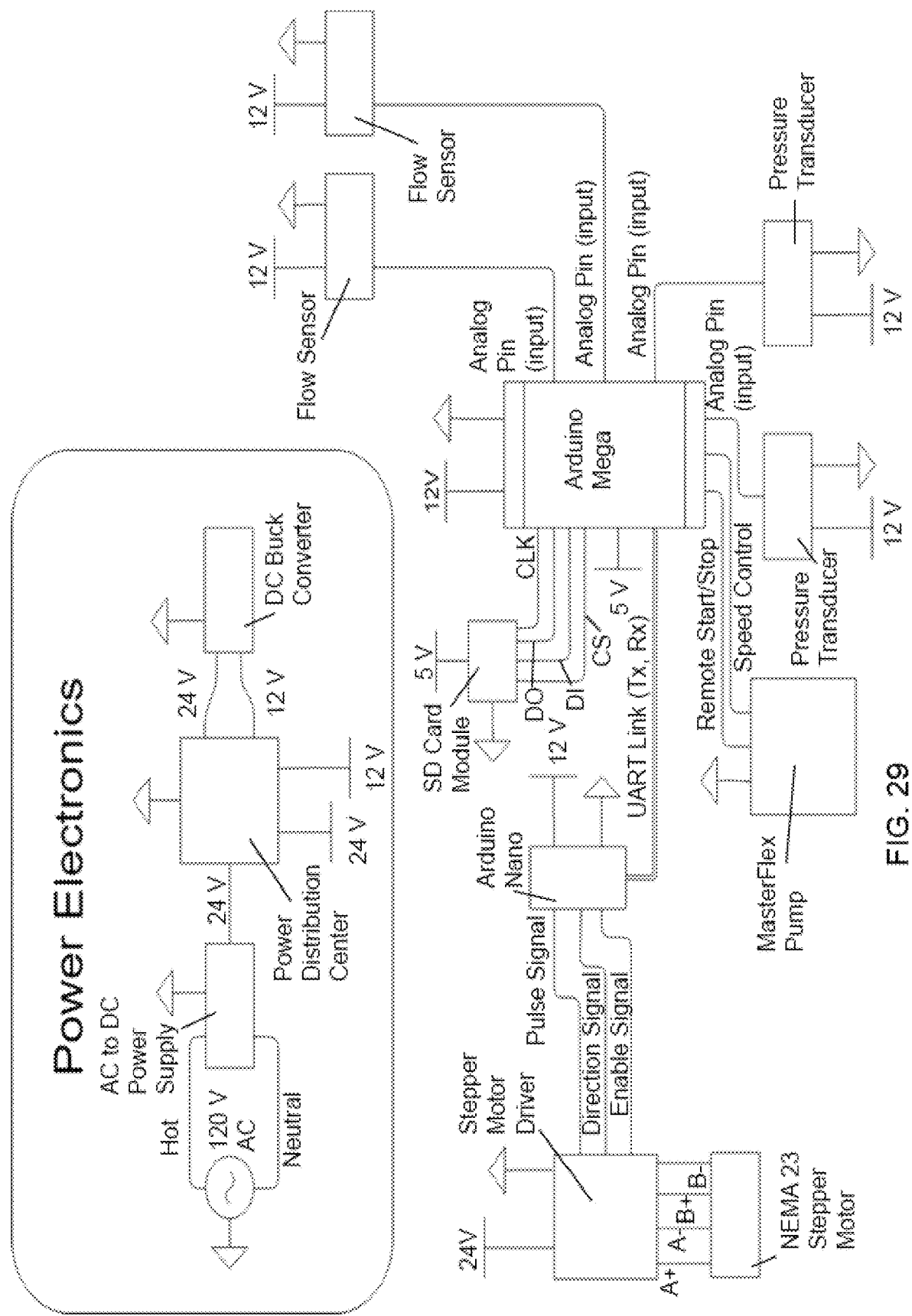

FIG. 29 is a diagram of an embodiment of a control system as described herein.

Figure 30:
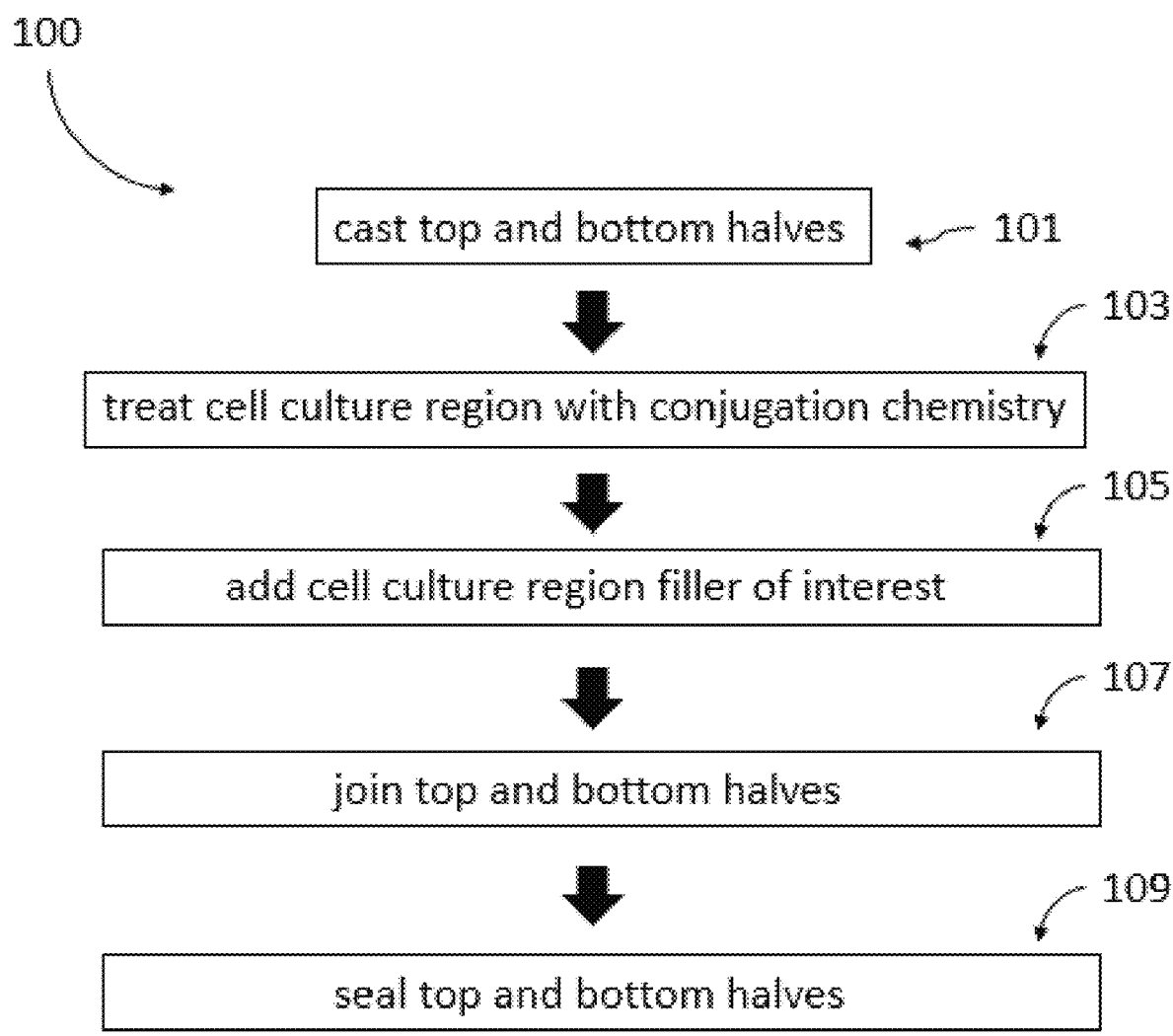

FIG. 30 is a flowchart of an embodiment of a method 100 of making a bioreactor as described herein.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used in the specification and the appended claims, the singular forms "a," "an," and "the" include plural referents unless the context clearly dictates otherwise.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

Embodiments of the present disclosure will employ, unless otherwise indicated, techniques of molecular biology, microbiology, cell biology, chemical engineering, mechanical engineering, physics, and the like, which are within the skill of the art. Such techniques are explained fully in the literature.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible unless the context clearly dictates otherwise.

Discussion

Current bioreactor devices capable of controlling fluid flow, stretching, and pressure are costly, use complex user interfaces, and remain black boxes. A sensing and automation system for a bioreactor device capable of autonomous control of fluid flow, stretching, and pressure in an affordable, user-friendly, and open-source manner while exceeding reliability and quality standards of the state-of-the-art is needed.

With that said, described herein are various embodiments of a bioreactor device and system that can have a single-body parallel-plate flow chamber that can be configured to be stretched/strained in one or more axes. The chamber can be configured to decouple strain from fluid flow and hydrostatic pressure while still allowing for the material properties experienced by the cells cultured in the chamber to be varied. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Described herein are various embodiments of a bioreactor system that can include a bioreactor chamber, a flow circuit, a support structure, and a control system. The bioreactor chamber can be fluidly and/or physically coupled to the flow circuit. The flow circuit and/or bioreactor chamber can be physically coupled to the support structure. The flow circuit, bioreactor chamber, and/or control system or component thereof can be physically coupled, electrically coupled, fluidly coupled, and/or otherwise in communication with the control system.

Figures 1A, 1B, 1C:
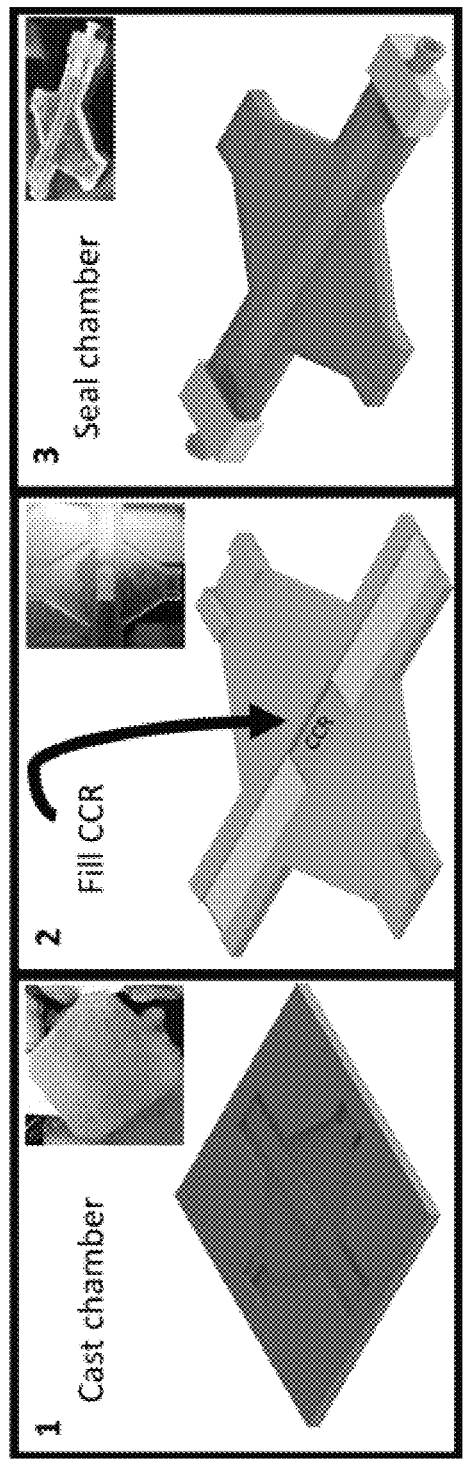
FIGS. 1A-1C are renders of chamber fabrication. First the Sylgarde 184 polydimethylsiloxane elastomer chamber halves are cast in molds (FIG. 1A). Then the "cell culture region" (CCR) is treated for bonding and the substrate filler material of interest is added (FIG. 1B). Two chamber halves are then glued together and sealed with our custom luer lock fittings to make a complete chamber (FIG. 1C).
Figure 2B:
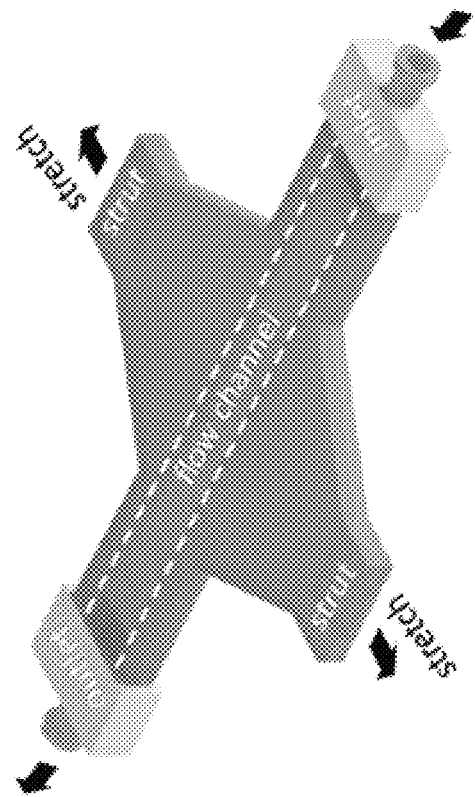
FIGS. 2A-2B are renders of the bioreactor chamber. A rectangular flow channel (dotted line of FIG. 2B) with a central region termed the CCR (shaded blue) runs through the chamber. Perpendicular to the flow channel are struts used for clamping and stretching the inner channel. The struts of each chamber half have inverse mechanical interlocks to facilitate alignment of the two halves during chamber fabrication. Arrows at the inlet and outlet fittings show the direction of fluid flow. Arrows at the struts show the direction of chamber displacement to create the region of well-defined strain.
Figure 2A:
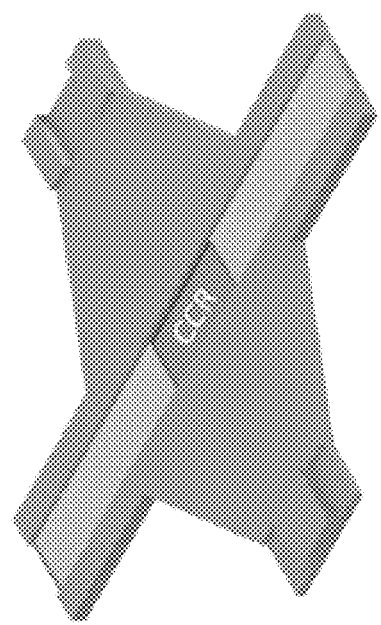

Discussion of the various components and embodiments of the bioreactor system described herein begins with FIGS. 1A-1C, FIG. 19, and FIGS. 21-23, which show embodiments of a bioreactor chamber and casting thereof as described herein. The bioreactor chamber can be configured generally as a single-body parallel-plate flow chamber. The bioreactor chamber can have a flow channel extending along a first axis (as shown in FIG. 2B, for example). The bioreactor chamber can be substantially symmetric with opposing inlets and outlets at either end of the flow channel. The bioreactor chamber can have two struts that are configured to couple to a bi-directional linear actuator and are each on opposing sides of the flow chamber along a second axis that is perpendicular to the first axis (FIGS. 2A-2B, FIG. 23). In some embodiments, the bioreactor chamber is stretchable in at least one dimension. The bioreactor chamber can also include a cell culture region (CCR) comprising a cell growth substrate. The cell growth substrate can be stretchable. In some embodiments the cell growth substrate is the bottom portion of the bioreactor chamber flow channel. The cell growth substrate can be coupled to the base of portion of the bioreactor chamber and coupled to or incorporated with the struts of the bioreactor chamber. The cell growth substrate can be placed in a cell culture region of a bioreactor as described herein. In embodiments, the cell growth substrate can further comprise a cell growth matrix. In further embodiments, the cell growth matrix can be conjugated to the cell growth substrate using conjugation chemistries Cells can be grown in a cell growth matrix that can be placed on the cell growth substrate. In some embodiments, a cell growth matrix can be placed in individual spots on the cell growth substrate. In some embodiments, the cell growth matrix is a gel matrix. In some embodiments, the cell growth matrix is a biomolecule matrix. In some embodiments, the cell growth substrate is a silicone substrate or a silicone rubber substrate or a citrate-based elastomer substrate or hydrogel substrate. In some embodiments the bioreactor chamber or portion thereof is composed of a silicone material or a silicone rubber material or PDMS [or another biocompatible elastomer]. The cell growth substrate can be any material that can bond to PDMS, deformable or not. If it is deformable, than it must have an elastic modulus less than that of the chamber.

The bioreactor chamber can have a cell culture region. The cell culture region can be a region within the flow channel or at least encompass an area of the flow channel. In some embodiments the cell culture region can be the width of the flow channel (e.g. about 10 mm), e.g. about 20 mm long with center at the center of the flow channel and about 1 mm deep. The flow channel dimensions can be scaled up and down according to the needs of the end user. The cell culture region dimension can be as wide as the flow channel. The cell culture region length should be no larger than 20 mm. The depth of the cell culture region should be no deeper than 1 mm.

Example materials which can be used to fill it are, silicones, polyacrylamides, collagen gels, poly(diol citrates), alginates, and polyacrylic acids. This can be done using benzophenone. The cell growth matrix (extracellular matrix proteins such as collagen, fibronectin, laminin or adhesion peptides such as RGD and YIGSR) can then be conjugated to the cell culture region filler material (cell growth substrate) using sulfo-SANPAH photocrosslinking chemistry or NHS-EDC carbodiimide chemistry.

In embodiments according to the present disclosure, the cell growth substrate can be a silicone substrate, a silicone rubber substrate, a citrate-based elastomer substrate, or hydrogel substrate.

In embodiments according to the present disclosure, the cell growth matrix can be one or more of silicones, polyacrylamides, collagen gels, fibronectins, poly(diol citrates), alginates, polyethylene glycol hydrogels, polyhydroxyalkanoates, hyaluronic acid hydrogels, or polyacrylic acids, individually or in combination. In some embodiments, the cell growth matrix is a biomolecule matrix comprising extracellular matrix proteins such as collagen, fibronectin, laminin or adhesion peptides such as RGD and YIGSR.

The cell growth matrix can be conjugated to the cell growth substrate using, for example, sulfo-SANPAH photocrosslinking chemistry or NHS-EDC carbodiimide chemistry or other suitable conjugation chemistries capable of reacting with a modified or unmodified PDMS surface and the desired cell culture substrate material. The skilled artisan would understand that the specific cross-linking chemistry to be employed would be one that is suitable depending on the particular cell growth substrate and cell growth matrix. Further conjugation chemistries that can be employed are described in the art, for example, in the textbook "Bioconjugate Techniques" authored by Greg T. Hermanson (published by Academic Press on Aug. 19, 2013), which is incorporated by reference in its entirety.

The bioreactor chamber can further comprise one or more transparent portions configured to provide an optical imaging path for a microscope to image the cell culture region, for example transparent glass on a top and bottom side of the cell culture region.

During operation, as the struts can be pulled on by the bi-directional linear actuator, the cell growth support substrate can be stretched in a direction that can be perpendicular to fluid flow such that a strain is applied to flow channel without causing lateral displacement of the cells within the flow channel. The operation of the bi-directional linear actuator can be such that an effective cyclical strain can be applied without lateral displacement. As shown in FIGS. 20A and 20B, the dimensions of the cross section of the bioreactor chamber can change as a bi-lateral stretch/strain is applied to the base or other support structure upon which cells may be grown. In this figure this is assuming that the strain in both directions is equal.

Additional features of embodiments of the bioreactor chamber can be appreciated in view of FIGS. 21-23. FIG. 21 shows a perspective view of the bioreactor chamber with the top half not shown. FIG. 22 shows a perspective view of the bioreactor chamber. FIG. 23 shows a perspective view of the bioreactor chamber with end caps in place. End caps can be included and configured to provide connection ports to facilitate coupling of the bioreactor chamber to the flow circuit. In some embodiments, the end caps can be configured to couple to tubing of the flow circuit. In some embodiments, the end caps can be configured as the male end of a Luer lock connector with the insert side having a barb to secure and seal it to the bioreactor chamber. Flow circuit tubing can connect to the end caps using a Luer lock connection. With this, an assembly of stopcocks can be integrated to allow for the chamber to be integrated into the flow circuit.

FIGS. 24A-24E show panel of contour plots of the total strain experienced by the bottom interior face of an embodiment of the flow channel (FIG. 24A) is at 0 s, (FIG. 24B) is at 0.25 s, (FIG. 24C) is at 0.50 s, (FIG. 24D) is at 0.75 s, and (FIG. 24E) is at 1.00 s. For this model, the problem was defined as Uniaxial stretching of the chamber to generate 10% strain in the center of the flow channel. The geometry of the chamber was defined as a symmetric structure with opposing inlets and outlets. Pulling on the struts at equal rates is to provide strain to the flow channel without lateral displacement such that the channel can be imaged by microscopy in-situ (FIGS. 1A-1C, FIG. 19, and FIGS. 21-23). In the embodiment, the chamber is 100 mm long, 90 mm wide, and 5 mm high. The geometry was meshed. An unstructured tetrahedral mesh was prepared as a first attempt for solving the transient structural problem. The mesh contained 35,860 elements and was refined using face sizing on the interior faces of the flow channel. Element sizing was capped at 2.5 mm for the main body and a face size of 1.0 mm was used for the interior faces of the flow channel. This was done to provide augmented spatial resolution of the flow channel deformation and strain field. A mesh independence study found that this mesh provided suitable accuracy of the strain field while minimizing computation time. The boundary conditions were then defined. The boundary conditions of the problem were applied to copy those expected to exist when the device is in service. To satisfy the 10% strain requirement for the design, the struts were each set to be displaced by 3.5 mm normal to the strut face following a linear ramp from 0 mm displacement to the full displacement in 0.5 s. Then the struts would be returned to their original position following the same linear ramp profile with the displacement directed in the opposite direction in 0.5 s. The two faces of the flow channel were set as fixed supports meaning that they would undergo zero deformation and displacement. The top and bottom of the chamber were set as frictionless supports meaning that they would undergo zero deformation but would allow lateral displacement. The transient structural analysis settings were largely left to be controlled by the program. These settings are selected to define the type of solver related to the physics of the problem as well as methods for ensuring convergence of the solution. The large deflection setting was turned on because silicone rubber is a hyperelastic material. The time step amounts were defined to ensure convergence of the solution. The solution results of the total strain for the bottom interior face of the flow channel were determined. The total strain was plotted as an overlaid contour plot on the chamber geometry at five time points over the course of the simulation (FIGS. 24A-24E). The total strain achieved was 10.849% after 0.50 s.

As previously described the bioreactor chamber can be coupled to a flow circuit. The flow circuit can be coupled to the inlet and the outlet of the bioreactor chamber. In some embodiments, the flow circuit can be coupled to end caps at the inlet and the outlet ends of the bioreactor chamber. The flow circuit can be fluidly and/or physically coupled to the bioreactor chamber. FIG. 25 is a diagram showing one embodiment of a flow circuit. The flow circuit can include tubing through which fluid can flow, the flow channel of the bioreactor, media reservoir(s), pump(s), dampener(s), sensor(s), pressure transducer(s), media port(s) and combinations thereof. The pump can be a peristaltic pump or any other suitable pumps. A hydrostatic linear actuator (FIG. 28) can be physically and/or fluidly coupled to the flow circuit. The sensor(s) can be coupled to or otherwise integrated with any component of the flow circuit. The sensor(s) can be configured to sense, detect, measure, and/or otherwise respond to one or more physical, chemical, and/or biological characteristics of the fluid flowing through the flow circuit and/or other parameter of the flow circuit, including but not limited to, temperature, flow rate, pH, turbidity, fluid pressure, and/or nutrients. The flow circuit can be a closed circuit. The flow circuit or any component thereof can be physically coupled, electrically coupled, or otherwise in communication with the control system.

In operation, the pump can circulate fluid through a conduit (e.g. tubing) across through the flow channel of the bioreactor chamber. Various sensors can measure characteristics of the flow circuit and can provide a signal or information to the control system. The control system can process the input signal and/or information and provide a control signal to one or more components of the flow circuit or other bioreactor system component (e.g. the bioreactor chamber, hydrostatic pressure linear actuator, and/or bi-directional linear actuator) to automatically operate the system based on operator input or guidelines (such as desired strain, flow rate, pressure, etc.).

As previously described, the bioreactor system can also include a bi-directional linear actuator that can be coupled to the struts of the bioreactor chamber and/or physically coupled, electrically coupled, or otherwise in communication with the control system. An embodiment of the bi-directional linear actuator is shown in FIG. 27. The bi-directional linear actuator can have support members configured to hold and strain the chamber and can be constructed from readily accessible, open-source parts. Motion is generated by a lead screw linear actuator. The chamber is strained from both ends so that it is possible to conduct live-cell imaging without side (lateral) movement. If the chamber was only pulled from one end, it would translate the cells across the microscope field of view. By pulling one both ends, the cells remain fixed in the microscope field of view while still being strained. A bi-directional lead screw is used to achieve coupled, uniform stretching of both sides. The chamber struts can each be clamped and pulled by a platform moving by the motion of the linear actuator.

The major component of the structure is the linear actuator. In embodiments, the bi-directional linear actuator can include a NEMA 23 stepper motor, bi-directional lead screw, and clamps. The bi-directional lead screw can provide a highly reliable and controllable motion. As the screw makes one complete revolution the translated distance of the connected piece is defined by the screw threading. A bi-directional lead screw connects two opposing screw threads together; one end is right handed while the other is left handed. This configuration allows for parts connected on either end to translate in opposite directions upon rotation of the screw. Likewise, the motion is coupled such that each component on either end translates the same amount if the threading is the same. In some embodiments, the bi-directional lead screw can have an 8 mm lead. The clamps can be height adjustable on the railing and can be spring-loaded for locking. They can be coupled to the railing using standard hardware. The spring-loaded mechanism can be achieved using small, stiff O-rings that elastically deform when extended and recoil to provide a load sufficient to lock the bioreactor chamber in the clamp.

As previously described, the bioreactor system can also include a hydrostatic pressure linear actuator as shown in FIG. 28. The hydrostatic pressure linear actuator can be coupled to the support structure of the bioreactor system. The hydrostatic pressure linear actuator can be and/or physically coupled, electrically coupled, or otherwise in communication with the control system. The hydrostatic pressure in the chamber is changed by varying the vertical height of the media reservoir with respect to the vertical position of the chamber. This is because the hydrostatic pressure acting on the cell culture region increases with an increase in the volume of fluid above it following equation 1.

$$P = \rho g h \tag{Eq. 1}$$

A second linear actuator with a right-handed lead screw can be included and used to control the position of the media reservoir bottle (FIG. 28). The media reservoir can be fluidly coupled to the flow circuit.

As previously discussed, the bioreactor chamber, the flow circuit, the bi-directional linear actuator, and the hydrostatic pressure linear actuator, and/or the control system or components thereof can be coupled to a support structure as shown in FIG. 26. The support structure can be configured to organize, support, secure, and position the various components of the bioreactor system appropriately. The support structure can form an organized frame and can be generated from open-source, commercially available components.

The bioreactor system described herein can further include a control system that can be coupled to or otherwise in communication with the bioreactor chamber, the flow circuit, the bi-directional linear actuator, and/or the hydrostatic pressure linear actuator or any component thereof. A diagram of an embodiment of a control system is shown in FIG. 29. In operation, a user can provide input parameters into the control system. As the flow circuit and bioreactor chamber is operated, data (e.g. signal data) regarding the fluid flow within the flow circuit, the flow circuit, the bioreactor chamber, the hydrostatic pressure linear actuator, and/or the bi-directional linear actuator is provided to and/or processed by the control system. The control system can then provide an appropriate signal to one or more components of the bioreactor system to control the conditions applied to cells in the bioreactor chamber in accordance with the input parameters provided by the operator.

In some embodiments, the control system can include a microcontroller that is capable of reading from multiple Pressure Transducers, Flow Sensors, and other sensors within the bioreactor system to automatically control a pump (e.g. a MasterFlex® Peristaltic Pump); while, also being able to control a motor (e.g. stepper motor to strain) a bioreactor chamber(s) in a controlled and precise manner. The control system can include a user interface. The user interface for the device can be user-friendly and allow operators to easily customize functionality without need for understanding the technical inner workings. The hardware and software for the design can be open-source and readily available.

As shown in FIGS. 4A-4B and FIG. 29, the control system can include power electronics that can allow the motor, flow sensors, pressure transducers, and other electronics to function properly. Power can be drawn from an AC outlet and then is transferred to the AC to DC Power Supply, which can use either 120V @ 60 Hz or 250V @ 50 Hz. Thus, it can work in anywhere in the world. The AC to DC Power Supply can convert the 120V AC wall outlet into a constant, 24V DC line, with a max current of 15 A. A voltage of 24 V can be used as that is the highest voltage required by the components, namely the NEMA 23 Stepper Motor and DQ542MA Stepper Motor Driver as shown in FIG. 29. Moreover, it is more efficient to step-down the voltage rather than step-up the voltage (otherwise known as boosting). The remaining components in some embodiments can require 12V. A DC to DC Buck Converter can be used to step down the 24V to 12V while further regulating the output signal. After stepping down the voltage, the power is distributed by the power distribution center (PDC). This can provide two isolated channels and protects each component from short-circuits and a high-current draw by using fuses. The PDC allows organization of the direction of power by labeling each power terminal, thus allowing for troubleshooting and monitoring all major electrical characteristics of the circuit, because the device has notification LEDs. The two voltage channels, 24V and 12V, share a common ground. The PDC can be composed of a 10-Way Fuse Block that acts as the ground to complete each circuit for the system. A series of small bus bars can be used to create the 24V and 12V channels. A SPST (Single Pole, Single Throw) switch can be used to turn on/off the Power Electronics safely without needing to unplug the AC cable; the switch can be connected in series with the AC input of the AC to DC power supply.

The Stepper Motor Driver can receive 24V from the PDC (which satisfies the voltage requirements for the NEMA 23 Stepper Motor and the Stepper Motor Driver) and then can use its 24V to power the NEMA 23 Stepper Motor. The linear actuator uses a NEMA 23 Stepper Motor with an operating voltage of 12-48 VDC and a max input current of 2.8 A/phase. For the Arduino Uno to interface with the Stepper Motor Driver, only three wires are required. In short, the Arduino Uno specifies the direction of rotation for the Stepper Motor (Direction Signal), whether the Stepper Motor should be on or off (Enable Signal) and the stepping amounts (Pulse Signal). The Arduino Uno's task is to control the stepper motor by sending a constant pulse signal to the stepper motor driver. The Arduino Uno receives its commands (frequency, amplitude, etc.) from the Arduino Mega via a serial interface (UART). The Arduino Uno can use 12V. The Arduino Mega can collect sensor data, acquiring user input, writing stepper motor commands to the Arduino Uno, and controlling the speed of the MasterFlex® pump. The Arduino Mega interfaces with the flow sensors, pressure transducers, and Arduino Uno through regular TX and RX (UART serial), and the Arduino Mega sends control commands to the MasterFlex® pump through a Digital to Analog Converter (DAC), as Arduino devices cannot output variable voltages between 0V and 5V. The MasterFlex®'s speed control uses analog voltages in this range and maps those values to a flow rate. The DAC uses I2C (synchronous data protocol) to receive voltage values. The Arduino Mega uses two I2C pins, Serial Data (SDA) and Serial Clock (SCK) to transfer the desired output voltage to the DAC, which then outputs the necessary voltage. The Arduino Mega can output a maximum of 800 mA from its regulated 5V pin, enough to control the pump.

The Adafruit VL6180X Time of Flight Distance Ranging Sensor is used to calibrate the system. The easiest way to acknowledge whether the stepper motor has moved to its destination is to use another device for feedback, such as a distance sensor connected to the Arduino Uno. The VL6180X is suitable for this task. This sensor is powered from the 3.3V output pin of the Arduino Uno and communicates with the Arduino Uno using I2C. This sensor can allow the system to start at the same point and move to a range defined by the user, then repeat this process with precision. The sensor can be mounted to one of the posts and can measure the distance between the two posts.

The SD card module can interface with the Arduino via Serial Peripheral Interface (SPI), which consists of a clock (CLK), data out (DO), data in (DI), and channel select, and its job is to write sensor data collected to the attached SD card. The Arduino uses its digital pins to act as the CLK, DO, DI, and CS lines. The SD card module can be powered by the 5V regulated supply provided by the Arduino Mega.

The DAC module can interface with the Arduino via I2C, and it converts digital voltage values into analog voltage values between 0V and 5V. The DA module can be powered by the 5V regulated supply provided by the Arduino Mega.

It will be appreciated that other configurations and components can be incorporated into the control system.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

Abstract:

Increasingly being recognized is the role of the complex microenvironment to regulate cell phenotype; however, the cell culture systems used to study these effects in vitro are lagging. The complex microenvironment is host to a combination of biological interactions, chemical factors, and mechanical stimuli. Many devices have been designed to probe the effects of one mechanical stimulus, but few are capable of systematically interrogating all combinations of mechanical stimuli with independent control. To address this gap, a novel bioreactor platform has been developed (an embodiment of which referred to herein as the Mechano-BioTester platform), which is a decoupled, multi-stimulus cell culture model for studying the cellular response to complex microenvironments in vitro. The system uses an engineered elastomeric chamber with a specially defined region for the incorporation of a different target material to act as the cell culture substrate. The system has been tested for several target materials including: polydimethylsiloxane elastomer, polyacrylamide gel, poly(1,8-octanediol citrate) elastomer, and type I collagen gel for both 2D and 3D co-culture settings. Additionally, when the chamber is connected to a flow circuit and the included stretching device, stimuli in the form of fluid flow, cyclic stretch, and hydrostatic pressure were able to be imparted with independent control. The platform has been validated using a combination of experimental and computational methods to define a known range of capabilities relevant to physiological microenvironments. The MechanoBioTester platform can function as a model system for mechanobiology, biomaterial design, and drug discovery applications that focus on probing the impact of a complex microenvironment in an in vitro setting.

1. Introduction

The human body experiences numerous interacting mechanical stimuli from the mechanical loading of the musculoskeletal system to the rhythmic loading of the cardiovascular system. In turn, tissue level stimuli are transferred to the cellular level such that the cells forming these tissue detect and respond to these mechanical stimuli via mechanotransduction pathways[1]. More specifically, cells exist in a 3D viscoelastic extracellular matrix through which they can be stimulated by external fluid flow, stretching, pressure, chemical factors, neighboring cells, and the properties of the matrix they inhabit. The complex microenvironment is the combination of these biological interactions, chemical factors, and mechanical stimuli. In recent years, the relative importance of mechanical stimulation to regulate cell phenotype has been revised to be on par with that of chemical factors.

To reach this point, many in vitro cell culture models have been developed to understand the mechanobiological response of cells to each individual mechanical stimulus. These devices have been designed to expose adherent cells to either fluid flow, cyclic stretch, or applied pressure[2-4]. And by using these systems, insights have been gained into cellular regulation, differentiation, and pathology[2,5,6]. An additional factor increasingly being recognized has been the effect of material properties for their contribution in regulating cellular function[5,7-11]. However, these historic devices for fluid flow, cyclic stretch, and applied pressure have relied on supraphysiologically stiff glass, silicone, or tissue culture polystyrene as the cell culture substrate. Moreover, these aged methods do not provide a method for stimulation by multiple factors to better recapitulate the cellular microenvironment in vitro. Only recently, has there been an effort to better emulate the in vivo microenvironment by developing systems to apply pairwise combinations of mechanical stimuli to cultured cells[4,5,12]. These devices and their results have been previously reviewed as they relate to the vascular microenvironment to draw attention to the synergistic and antagonistic effects in cellular response when cells are stimulated by pairs of mechanical stimuli[5,12]. Despite their significant interaction, few have further investigated combinations of more than two mechanical stimuli[13-16]. One explanation for this is that these systems are traditionally complicated, confounded, and material-specific. Additionally, many of these devices are built in-house and are lab-specific. Because no standard device is used for mechanical stimulation studies, it is difficult to compare results as each device and stimulation mechanism has its own benefits and limitations. A cell culture model capable of applying all combinations of mechanical stimulation with independent control of each stimuli would reduce this experimental variability.

Furthermore, cells interact with other cell types in vivo and the need to capture this effect is growing. Using an organ-on-a-chip model has revealed unique interactions between endothelial and lung epithelial cells exposed to cyclic strain[17]. To date, endothelial cell and vascular smooth muscle cell co-culture has been studied under static conditions or under limited mechanical stimulation (principally fluid shear stress) in 2D or 3D settings; however, these cell types are additionally exposed to cyclic stretch and hydrostatic pressure[19]. A system capable of stimulating cells in co-culture would enable a greater understanding of biological and mechanical interactions in regulating cellular phenotype.

Thus, to further probe the complex microenvironment in vitro, it is necessary to have a system for independently controlling mechanical stimulation. Described herein is a novel bioreactor platform, the MechanoBioTester, which is an embodiment of a custom-built system engineered to decouple the effects of fluid flow, cyclic stretch, hydrostatic pressure, and material properties for their independent control and application in combination. This system relies on a chamber specific for this purpose and a complementary series of equipment to support its functionality. The device has been validated using a combination of experimental and computational methods to define a known range of tested capabilities relevant to physiological microenvironments. This platform has the ability to function as a cell culture model for mechanobiology, biomaterial design, and drug discovery applications that focus on probing the impact of complex microenvironments in an in vitro setting.

2. Materials & Methods 2.1. Chamber Fabrication. The central chamber is composed of two separate halves that are fused together. The top and bottom halves of the chamber were fabricated by casting polydimethylsiloxane elastomer (PDMS) (Dow Sylgard 184, 10:1 base to curing agent) into custom designed molds, degassing, and curing at 70° C. for 2 hours followed by sonicating in 70% ethanol solution for 10 minutes. After demolding and drying, the inset cell culture region (CCR) was prepared for bonding the material substrate of interest (FIGS. 1A-1C). Chamber assembly was designed to be a straightforward process: 1) cast the chamber (FIG. 1A), 2) fill the CCR (FIG. 1B), 3) seal the chamber (FIG. 1C).

2.1.1. CCR Substrate: Polydimethylsiloxane elastomer (PDMS). To achieve the experimental working range of elastic moduli, Dow® Sylgard™ 184 and Dow® Sylgard™ 527 were mixed separately according to the manufacturer's instructions and then mixed together according to the ratios described by Palchesko et al[20]. The CCR was then filled with the mixture and degassed. To impart a surface roughness to the PDMS, an abraded Plexiglas coverslip was placed in contact with the uncured PDMS in the CCR. The coverslip extended beyond the length of the CCR to prevent its sinking into the uncured PDMS during curing. The assembly was then baked at 70° C. for 1 hour. Next, all chamber parts were sterilized by steam autoclaving at 121° C. for 20 minutes. All further work was conducted aseptically in a biosafety cabinet. Adapting the methods of Li et al., the filled CCR was then functionalized with 2 mM sulfo-sulfosuccinimidyl 6-(4'-azido-2'-nitrophenylamino)hexanoate (sulfo-SANPAH; ThermoFisher Scientific) diluted in sterile deionized water and afterwards incubated overnight with 400 µL of either 0.1 mM RGD peptide (abcam) diluted in sterile deionized water or 0.4 µM vascular endothelial growth factor (VEGF) receptor-2 binding DNA aptamer with a 5' amine functionality (Integrated DNA Technologies) diluted in sterile deionized water[21,22]. The chamber was then formed by gluing the top and bottom parts together with PDMS (Dow® Sylgard™ 184, 10:1 base to curing agent) and cured at 37° C. overnight. Chamber sealing was also completed using ReproRubber® Thin Pour (ReproRubber®) a two-part platinum catalyzed, addition cured silicone, which cures in ~10 minutes at room-temperature after mixing. For gluing, either of the uncured silicones were applied as a thin layer to the contact area of one chamber half using a micropipette tip. Sufficient phosphate-buffered saline (PBS; Corning) in the form of a droplet was left in the chamber during gluing to keep the conjugated chemistries hydrated for the remaining fabrication processes. Next, the seam formed by the joined chamber parts was coated in a thin layer of PDMS (Dow® Sylgard™ 184, 10:1 base to curing agent) and again cured at 37° C. overnight. This sealing process was also achieved using ReproRubber® Thin Pour and only required 10 minutes for curing at room-temperature. Then custom 3D printed luer lock fittings were inserted into the chamber openings, sealed to the chamber using PDMS (Dow® Sylgard™ 184, 10:1 base to curing agent), and cured at 37° C. overnight. Fittings were also able to be sealed using ReproRubber® Thin Pour, which was allowed to cure for 10 minutes at room-temperature. This sealing procedure was necessary to ensure a water-tight chamber.

2.1.2. CCR Substrate: Polyacrylamide gel (PA). The CCR of the chamber was prepared for bonding PA to PDMS by impregnating the PDMS surface with benzophenone (Sigma-Aldrich), a UV photoinitiator, following the methods of Simmons et al[23]. PA precursor solution was prepared by mixing acrylamide solution (Bio-Rad), bis-acrylamide solution (Bio-Rad), tetramethylethylenediamine (Bio-Rad), and ammonium persulfate (Sigma-Aldrich) following the protocol of Fischer et al[24]. The mechanical properties of the polyacrylamide were controlled by varying the relative concentrations of acrylamide and bis-acrylamide in the precursor solution. Immediately after benzophenone treatment, the CCR was filled with PA precursor solution, a Plexiglass coverslip was placed over the CCR, and it was allowed to gel polymerize under a handheld UV-lamp emitting at a wavelength of 365 nm for 45 minutes in a biosafety cabinet. This process was to both bond the two materials together and UV-sterilize the chamber halves by conducting the step in the biosafety cabinet[25]. In a similar manner as for PDMS, a surface topography was transferable to the PA by using an abraded Plexiglas coverslip. All remaining steps were conducted aseptically in a biosafety cabinet. Following gel polymerization, the coverslip was removed, and the part was equilibrated in sterile phosphate-buffered saline (Corning) overnight. The PA filled CCR was then able to be functionalized using sulfo-SANPAH, the chamber halves glued, and afterwards sealed in the same manner as that for a PDMS filled CCR.

2.1.3. CCR Substrate: Poly(1,8-octanediol citrate) elastomer (POC). POC elastomer was synthesized following the protocols of Yang et al[26]. Briefly, 1,8-octanediol (Sigma-Aldrich) and citric acid (Sigma-Aldrich) were combined in an equimolar ratio and melted at 165° C. Upon complete melting, the temperature was reduced to 140° C. for the polycondensation reaction to proceed. The resulting viscous pre-polymer melt was purified by recrystallization in water and the purified pre-polymer was dissolved in ethanol to make a 50 wt % solution. This solution was then added to the CCR and the ethanol was allowed to evaporate. This process was repeated until the CCR was filled with POC pre-polymer. Subsequently, the filled CCR was baked at 80° C. for 2 days to thermally crosslink the POC pre-polymer to form the POC elastomer. The chamber was then glued together and sealed in the same manner as that for a PDMS filled CCR. POC supports cell adhesion on its own and thus surface functionalization was not carried out for the substrate. Complete chambers were gas sterilized using ethylene oxide.

2.1.4. CCR Substrate: Type I collagen gel (Col). All chamber parts were first sterilized by steam autoclaving at 121° C. for 20 minutes. All remaining steps were conducted aseptically in a biosafety cabinet. The unfilled CCR was functionalized with 2 mM sulfo-SANPAH (ThermoFisher Scientific) as previously described. The CCR was then filled with 400 µL of PureCol® EZ Gel type I collagen gel (Advanced Biomatrix) and incubated for 2 hours at 37° C. to allow the collagen solution to gel. The chamber was then glued together and sealed in the same manner as that for a PDMS filled CCR. For 3D culture, cells were mixed into the collagen solution prior to its addition to the CCR.

2.2. Simulation. Fluid-structure interaction (FSI) simulations were conducted using ANSYS Workbench 19.1 with the transient Mechanical and Fluent engineering simulation software packages. When necessary, computational time was reduced by modeling half the chamber using symmetry conditions across the center plane through the flow channel. The geometry for the mechanical simulations used an independent unstructured tetrahedral mesh that was refined at the chamber interior walls. The chamber material properties were those for silicone rubber provided in ANSYS. For a PA filled CCR, the material was considered homogeneous and linear elastic with an elastic modulus of 100 kPa and a Poisson's ratio of 0.45. Boundary conditions in the mechanical simulation were specified to outwardly displace the chamber struts following a squared sinusoidal wave with an amplitude ranging from 0-5 mm and a frequency of 1 Hz. The faces of the inlet and outlet of the chamber were fixed. An FSI boundary condition was assigned to the interior walls of the chamber. The geometry for the fluid flow simulations used an independent unstructured tetrahedral mesh. This was because a structured mesh resulted in negative volumes during the deformation due to the size of the timestep. Smaller timesteps were found to be too computationally exhaustive-severely increasing the time to complete the simulation. The fluid properties were those for cell culture media[27]. The boundary conditions were no-slip walls, either a steady or unsteady inlet velocity, and a standard 0 gauge pressure outlet condition. The walls of the fluid geometry were assigned dynamic mesh motion using the FSI specification. The Workbench system coupling module was used to one-way couple the mesh deformation of the structural simulation to the fluid flow simulation i.e. the mechanical simulation was used to inform the dynamic mesh motion in the fluid flow simulation at every timestep. One-way coupling was used because the range of hydrostatic pressure generated was found to negligibly deform the chamber. Following the simulation, the CFD-post module was used to visualize the results.

2.3. Attenuated Total Reflectance Fourier Transform Infrared Spectroscopy (ATR-FTIR). Functionalization of the PDMS filled CCR surface by peptide and DNA aptamer was confirmed by infrared spectroscopy. ATR-FTIR spectra were obtained using a Thermo Scientific Nicolet 6700 spectrometer with an MCT-Diamond window. Measurements were collected with a 4 cm$^{-1}$ resolution from 650-4000 cm$^{-1}$ and averaged over 32 scans.

2.4. Digital Image Correlation (DIC) Strain Mapping. The strain field in the CCR from stretching the chamber was determined by digital image correlation methods. To produce a speckled pattern for tracking, charcoal powder was mixed into the PDMS, PA, POC, and collagen prior to curing/gelation/polymerization and filling of the CCR. A USB digital microscope (Celestron) was used to record the CCR while the chamber was stretched. The recorded frames were then analyzed using a modified version of the Digital Image Correlation and Tracking with MATLAB code to calculate the directional and equivalent strains as calculated in the ANSYS software for comparison between the simulated strain and the measured strain[28].

2.5. Cell Culture. Human umbilical vein endothelial cells (HUVECs) (LifeLine Cell Technology®) were cultured at passage number 6 in complete VascuLife® VEGF Endothelial Medium (LifeLine Cell Technology®). Cells were passaged using cell dissociation buffer (Gibco) and seeded at 10,000 cells/cm$^2$ onto the functionalized PDMS substrates. Cell dissociation buffer was used to maintain the cell surface proteins necessary for adhesion. Representative images were taken and processed using the NIH ImageJ software. Green fluorescent protein expressing human umbilical vein endothelial cells (GFP-HUVECs) (Angio-Proteomie) were cultured at passage number 8 in Endothelial Growth Medium (Angio-Proteomie). Cell suspensions were seeded at a density of 10,000 cells/cm$^2$ into a completed chamber. The GFP-HUVECs were allowed to attach for 4 hours before further chamber manipulation. The chamber was then flushed and rinsed with phosphate-buffered saline (Corning) to remove unattached cells. Subsequently, the chamber was filled with Endothelial Growth Medium. The chamber was then connected to the flow circuit for use in the bioreactor system. For co-culture experiments, human aortic smooth muscle cells (AoSMCs) (Cell Applications) were cultured at passage number 8 in complete Human Smooth Muscle Cell Growth Media (Cell Applications). During passaging, the AoSMCs were labeled with Cell Proliferation Staining Reagent—Orange Fluorescence—Cytopainter (Abcam®) to make the cells visible in the gel while imaging. AoSMCs were then mixed into the PureCol® EZ Gel type I collagen gel (Advanced Biomatrix) solution at 500,000 cells/mL and used to fill the CCR as previously described in section 2.1.4. After gelation, 200 µL of Human Smooth Muscle Cell Growth Media was pipetted onto the gel to saturate it. The AoSMCs were allowed to attach within the gel overnight. Following, GFP-HUVECs were seeded on top of the gel at a density of 30,000 cell/cm$^2$ and allowed to attach for 4 hours prior to completing chamber fabrication. A 1:2 ratio of AoSMC to GFP-HUVEC media was used for the rest of the co-culture after initial seeding. Prior to imaging, live cell nuclei were labeled with Hoechst 33342 solution (ThermoFisher Scientific) following the manufacturer's instructions. Fluorescence images of chamber cross-sections were taken using a Nikon TE-2000 inverted fluorescence microscope and processed using the NIH ImageJ software.

3. Results 3.1. Overview: The MechanoBioTester is a Decoupled, Multi-Stimulus Cell Culture Model. This newly developed cell culture model is capable of independently varying flow regime, fluid shear stress, unidirectional cyclic stretch, hydrostatic pressure, and substrate properties for the systematic testing of all combinations of these stimuli in vitro (Table 1). Independent variation of stimuli means; for example, that the flow rate can be adjusted without changing the other stimuli conditions or the stretching conditions can be changed without affecting the flow rate and is not dependent on the material system used. Moreover, the system features the ability to test these conditions in both 3D and co-culture settings. We have tested the capabilities presented herein; however, the system is not limited to these values.

TABLE 1

Capabilities of the MechanoBioTester Cell Culture Model

| Stimulus | Capability | In vivo Property |
|---|---|---|
| Substrate Material[§] | Polydimethylsiloxane elastomer (PDMS) Polyacrylamide gel (PA) Poly(1,8-octanediol citrate) elastomer (POC) Type I collagen gel (Col) | Tissue-specific ECM |
| Substrate Modulus | 5-1500 kPa (PDMS)[20] 0.1-100 kPa (PA)[29, 30] 1850-6440 kPA (POC)[31] 0.1-20 kPa (Col)[32, 33] | Brain: ~1 kPa[7, 34] Muscle: ~10 kPa[7, 34] Collagenous bone: ~100 kPa[7, 34] Blood vessel: 8-100 kPa[35] |
| Substrate Topography | Isotropic or Anisotropic | Tissue-specific ECM architecture[36, 37] |
| Flow Regime | Laminar or Disturbed Unidirectional or Reciprocating | Straight blood vessel: Laminar/Unidirectional[38] Curved/bifurcated blood vessel: Disturbed/Reciprocating[38] |
| Fluid Shear Stress | 0-2* Pa | Blood vessel average: 1.5 Pa[38] |
| Cyclic Stretch | 0-15% strain 0-2 Hz | Blood vessel: 2-10%, 1 Hz[5, 6] Lung alveoli: 5-15%, 0.2 Hz[39, 40] Articular cartilage: 5-10%, 0.1-1 Hz[41] |
| Hydrostatic Pressure | 0-4⊥ kPa 0-2 Hz | Blood pressure: 0-16.5 kPa[5] Lung pressure: 0.2-2.5 kPa[40] |

[§]Included are only the materials we have tested; it is expected that more materials are also possible.
*Upper limit dependent on peristaltic pump and fluid properties.
⊥Upper limit dependent on greatest height of any flow circuit component.

The device centers around a novel, deformable, polydimethylsiloxane elastomer (PDMS) chamber, which is approximately 100 mm×100 mm×5 mm (FIGS. 2A-2B). The chamber was fabricated in PDMS because of the material's biocompatibility, elasticity, low-cost, optical transparency, and formability. Through the center of the chamber is a 10 mm wide, 2 mm high, and 100 mm long rectangular flow channel. The length of the channel was optimized to ensure steady, laminar flow developed without effects from the inlet and outlet. The chamber geometry was engineered to include a pair of struts perpendicular to the flow channel direction. These are for clamping and displacing to elicit a predictable strain field at the center of the flow channel. Additionally, the struts include interlocks to ensure alignment of chamber halves during fabrication to reduce chamber-to-chamber variability. Located at this central position is a 10 mm wide, 1 mm deep, and 20 mm long inset in both the top and bottom walls of the flow channel, termed the cell culture region (CCR) (FIGS. 2A-2B). This inset provides a region for introducing materials of interest different from that of the PDMS chamber. The CCR is fillable with any material capable of physically or chemically bonding to PDMS. A complete chamber is formed by sealing two chamber halves together and affixing our custom, biocompatible, 3D printed luer lock fittings (FIGS. 15A-15B). Two different silicone formulations were tested for sealing the chamber halves together: Sylgard®184 and ReproRubber® Thin Pour. Each had their specific advantages and disadvantages. Sylgard®184 was useful because it is optically transparent; however, it takes approximately 24-48 hours to fully cure at 37° C. Whereas, ReproRubber® Thin Pour cures in 10 minutes at room temperature drastically reducing fabrication time; however, it cures green, which can introduce minor background fluorescence near the walls of the chamber during fluorescence microscopy.

Figure 3A:
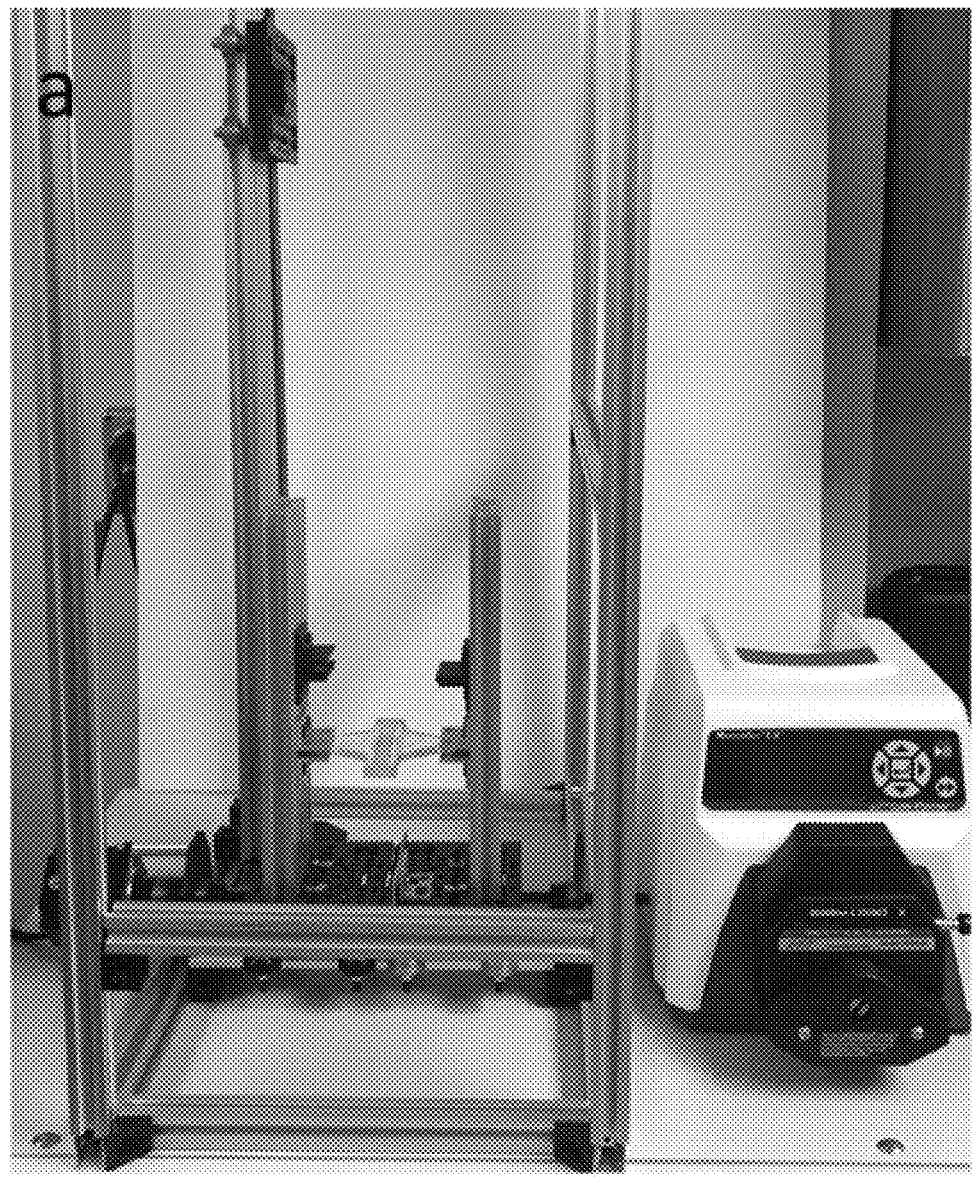
FIGS. 3A-3C is a photograph of a reduced to practice embodiment of the present disclosure, the Mechano-BioTester system. The system setup (FIG. 3A) is a flow circuit (circuit diagram of an embodiment in FIG. 3B) comprising media reservoirs, a peristaltic pump, a pulse dampener, an in-line pressure transducer, and the bioreactor chamber. The peristaltic pump can be used to generate flow and the dampener can be to minimize the intrinsic pulsatility in the flow rate from the pump. The media reservoir kept in the cell culture incubator is to ensure proper temperature and gas exchange of the flowing cell culture media. While the other media reservoir is used for adjusting the hydrostatic pressure in the chamber by changing its relative height with respect to the chamber. The in-line pressure transducer can be used to monitor the pressure in the chamber. The chamber stretcher can be a bidirectional lead screw linear actuator, which clamps onto the struts of the chamber (shown in the photograph of FIG. 3C).
Figure 3B:
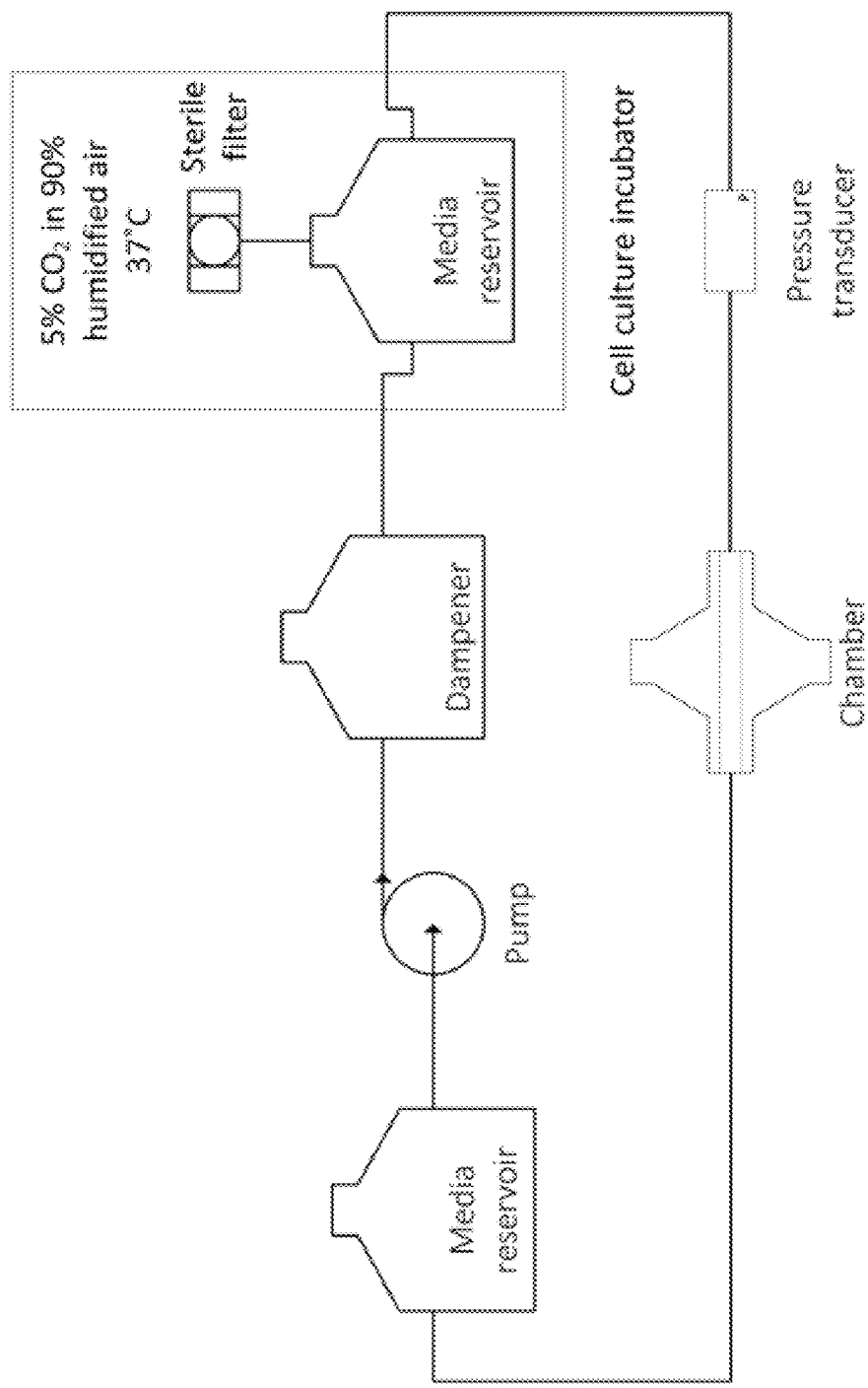
Figure 3C:
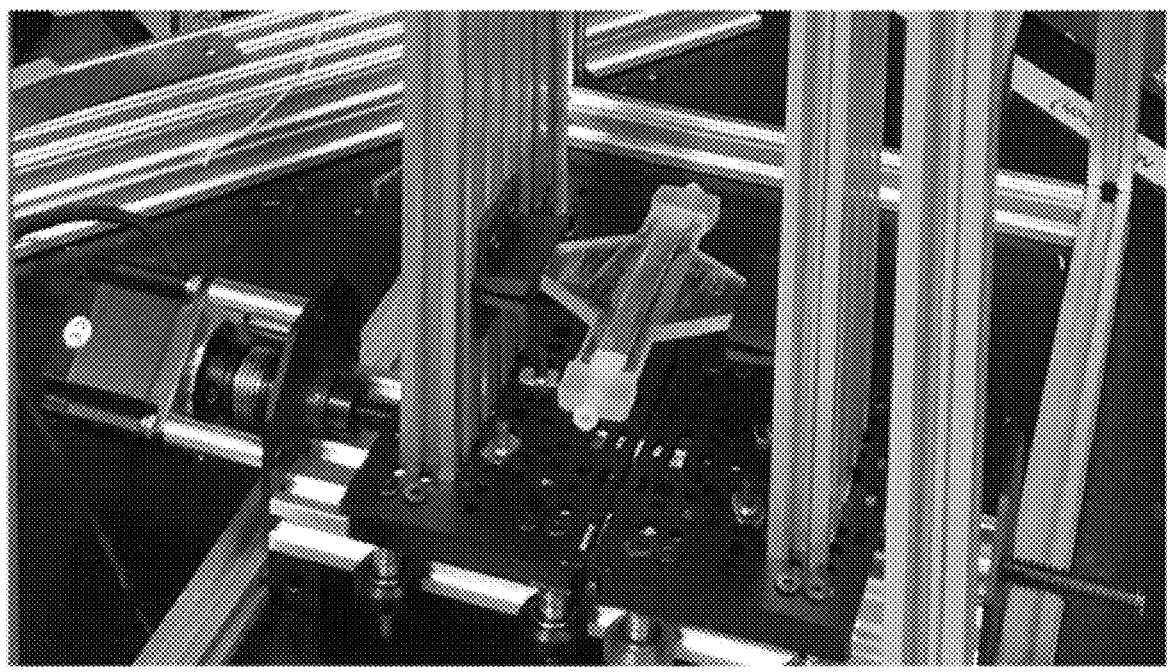

The chamber is then able to be transferred to the system frame, which houses the flow circuit and chamber stretcher (FIG. 3A). The flow circuit comprised a peristaltic pump, two media reservoirs, a pulse dampener, and an in-line pressure transducer (FIG. 3B). One media reservoir was placed in a humidified, 5% $CO_2$ cell culture incubator at 37° C. to maintain cell culture media pH and temperature. The second media reservoir was attached to a meter long vertically oriented linear actuator to control the hydrostatic pressure in the chamber. The chamber stretcher is a bidirectional lead screw actuator with clamps for securing to the chamber struts (FIG. 3C). The chamber stretcher works such that, as the lead screw rotates, the clamps mechanically move together or apart at the same rate to stretch the chamber. Thus, the deformation of the chamber is symmetric about the chamber centerline, which facilitates live-cell imaging because the image does not move out of the field of view.

A DinoLite USB microscope with 480/510 nm and 570/610 nm excitation/emission capabilities was incorporated to image the CCR in real-time using fluorescent protein expressing or fluorescently-labeled cells (FIG. 16). The peristaltic pump, linear actuators, and sensors were all connected to our custom, open-source control box (FIG. 4A). A series of three Arduino microcontrollers were used to coordinate the different electronic components and record sensor data (FIG. 4B). The MechanoBioTester system was designed to be a single device for mechanically stimulating cells in culture by combinations of material properties, fluid flow, cyclic stretch, and hydrostatic pressure.

3.2. Material Validation: We Successfully Bonded Biocompatible Synthetic Polymers and Natural Matrices to the Chamber. To demonstrate the system's material functionality, four different established chemistries were bonded to the CCR. First, the CCR was filled with different PDMS elastomer formulations to show that the simplest filler material was possible. It was then confirmed that polyacrylamide gel (PA), a tunable material used for mechanobiology experiments, could bond to the CCR as well. This was done by grafting the PA during its polymerization process to the PDMS by forming radicals at the surface layer of the PDMS. Radicals were formed using the photoinitiator benzophenone, which was first embedded in the surface of the PDMS and activated by UV irradiation during the PA polymerization process. To demonstrate the systems applicability to biomaterial development, it was demonstrated poly(1,8-octanediol citrate) elastomer (POC), a hemocompatible biomaterial, could bond to PDMS. POC is a sticky polymer and was capable of forming a sufficiently strong physical bond with PDMS without additional treatment to either material. The final material bonded to the CCR was a type I collagen gel (Col) to show that the MechanoBioTester system was not limited to synthetic, 2D material systems, but that natural, 3D matrices were also supported. To do this, the heterobifunctional crosslinker sulfo-SANPAH was used to chemically link the two materials together. The crosslinker's nitrophenyl azide group was first reacted with the PDMS CCR surface by UV irradiation to non-specifically insert itself into PDMS methyl groups. Then the exposed, surface bound sulfo-NHS esters from the sulfo-SANPAH were used to non-specifically react with primary amines on the collagen as it gelled. Successful bonding of these various materials broadens the cell culture model's applicability for investigating mechanobiology and cell-material interactions.

Moreover, topographies could be transferred to the material within the CCR during the material's polymerization process. This functionality was shown by transferring a uniform surface roughness to a PA filled CCR using an abraded Plexiglas coverslip during gel polymerization (FIG. 17A-17D). Because the chamber is flexible, it is possible to peel it away from a rigid mold, enabling more complex topographies to be transferred by micro-molding using etched silicon wafers. The CCR allows the system to be used for testing a variety of materials independent of the PDMS chamber.

3.3. Flow Validation: The Flow Channel Mimics a Parallel-Plate Flow Chamber. To determine the flow characteristics of the chamber, computational fluid dynamics (CFD) simulations were performed. The flow in the chamber assumed a steady, well-developed laminar flow field over the CCR (FIG. 5A). The fluid shear stress or wall shear stress (WSS) over the CCR was shown to vary linearly with the fluid flow rate. As expected, these results matched the theoretical solution of the Navier-Stokes equation for a parallel-plate flow chamber because the chamber geometry is a simple rectangular channel (FIG. 5B). Additionally, by partially filling the CCR to form a step feature, recirculating flow was shown to develop (FIG. 18). The simple flow channel geometry enabled the development of controllable flow characteristics.

3.4. Strain Validation: The Bonding of PDMS, PA, POC, and Collagen to the CCR Was Sufficient to Transfer Strain to These Materials. To confirm the strain field in the CCR for the different bonded materials, we employed digital image correlation (DIC) particle tracking methods[42]. From these measurements we calculated the average equivalent strain using the equation, $$\varepsilon_{eq} = \frac{1}{\sqrt{2}\,(1+v)}\left[(\varepsilon_x - \varepsilon_y)^2 + \varepsilon_x^2 + \varepsilon_y^2 + \frac{3}{2}\gamma_{xy}^2\right]^{\frac{1}{2}} \qquad \text{(eq. 2)}$$

in which $\varepsilon_{eq}$ is the equivalent strain, $v$ is the material's Poisson's ratio assumed to be 0.5, $\varepsilon_x$ is the strain in the x-direction, $\varepsilon_y$ is the strain in the y-direction, and $\gamma_{xy}$ is the shear strain. As expected, the strain varied linearly with strut displacement (FIG. 6). Furthermore, the variability of the strain in the CCR was minimal and consistent for a sinusoidal displacement profile (FIG. 6). We also performed ANSYS mechanical simulations of the stretched chamber, which agreed well with the experimental results. The simulation results showed more clearly the strain field that developed over the entire chamber geometry. The simulations revealed a near-uniform strain field in the CCR (FIG. 7A) and both the simulated and measured CCR average equivalent strain matched (FIG. 7B) with deviations only at larger strut displacements (>4 mm). Using the chamber stretcher, the stretching mechanism was made independent of both flow and pressure.

3.5. Pressure Capability: To Modify the Hydrostatic Pressure in the Chamber the Media Reservoir Was Mounted to a Separate Linear Actuator. To measure the hydrostatic pressure in the chamber, a PendoTech in-line pressure transducer was connected to the inlet of the chamber and kept level with the chamber. By raising or lowering the media reservoir, the hydrostatic pressure in the chamber was able to be increased or decreased independent of the flow and stretching mechanisms. As expected, the hydrostatic pressure varied linearly with changes in the media reservoir height according to the relationship:

$$P = \rho g h \qquad \text{(eq.3)}$$

where P is the hydrostatic pressure in the chamber, $\rho$ is the density of the fluid taken as 1000 kg/m$^3$ for water, g is the acceleration due to gravity taken as 9.799 m/s$^2$ in Gainesville, FL, and h is the relative height difference between the chamber and the media reservoir (FIG. 8A). Moreover, transient pressure profiles were produced by dynamically moving the media reservoir with the linear actuator (FIG. 8B). By using controlled height differences in the flow circuit, the hydrostatic pressure in the chamber was made independent of the flow and stretching mechanisms.

3.6. Fluid-Structure Validation: Simulations Revealed Optimized Conditions for Decoupling the Fluid Flow and Stretch Interactions in the Chamber. To understand the interactions occurring in the chamber, extensive fluid-structure interaction (FSI) simulations were performed. When the chamber is stretched this causes changes to the flow channel dimensions, which consequently influences the flow through the channel. As the chamber struts are pulled, the flow channel widens causing a vacuum effect pulling in more fluid and thus negatively spiking the flow rate through the channel. Then as the struts are returned to their initial position, the channel narrows to its original dimensions causing a pumping effect pushing out more fluid and thus positively spiking the flow rate through the channel. For that reason, it appeared the flow and stretch remained coupled. This was overcome by dynamically changing the flow rate to compensate and negate this fluid-structure interaction. Both steady and unsteady inlet flow rates were tested to determine an inlet flow rate function that minimized the variability of the WSS over the CCR. From the simulations, a steady inlet flow rate and a stretching profile imparted a sinusoidal-esque waveform on the WSS at the center of the CCR (FIG. 9A). This same sinusoidal-esque waveform was observed by the PendoTech in-line pressure transducer (FIG. 9B). Upon recognizing this, the effect of using an inlet flow rate with a sinusoidal waveform of the type, $$Q_{in} = Q_{ave} - A\,\sin(\omega t - \phi) \qquad \text{(eq. 4)}$$

was used, where $Q_{ave}$ is the average inlet flow rate over the stretching period, A is the flow rate $Q_{ave}$ amplitude, $\omega$ is the frequency, and $\phi$ is the phase angle between the cyclic stretch waveform and the flow rate waveform. It was found for a given displacement that the variability of the WSS at the center of the CCR was minimized by a phase angle of ~90° and a ratio of $$\frac{A}{Q_{ave}}$$

of ~4 for a waveform of this type and a cyclic stretching amplitude of 3.5 mm of strut displacement (FIGS. 10A-10B). The ratio of $$\frac{A}{Q_{ave}}$$

to minimize the WSS variability decreased with decreasing strut displacement. Simulation videos further illustrate the reduced variability in WSS by using these optimized parameters.

3.6. Biovalidation: The CCR Was Functionalized with Diverse Chemistries to Support Cell Attachment and Was Designed to Enable 3D, Co-Culture Studies. To further demonstrate chamber functionality, different chemistries were conjugated to facilitate cell attachment to the CCR filler material surface using the heterobifunctional conjugation chemistry, sulfo-SANPAH (SSP). The adhesion peptide sequence arginine-glycine-aspartate (RGD) and DNA aptamer were conjugated. Their conjugation to the surface was confirmed by attenuated total reflectance Fourier transform infrared spectroscopy (ATR-FTIR). This was observed in the absorbance spectra by the presence of a broad peak centered at 3500 cm$^{-1}$ corresponding to the stretching of the N—H bond of the amine groups found in all three species and not the substrate material, PDMS (FIG. 11A). Human umbilical vein endothelial cells (HUVECs) were shown to readily attach and spread to the functionalized PDMS surface after conjugation of the two chemistries (FIG. 11B). Conjugation to PDMS using SSP was shown, though this chemistry and others can be used to conjugate these same species to PA and POC. By using established conjugation chemistries, cell culture model systems as described herein can be a platform for studying the interactive effects of surface chemistry and ECM composition with mechanical stimulation on cellular behavior.

Using SSP, a Type I collagen gel was bonded to the CCR inset to form a 3D collagen matrix to demonstrate the system is not limited to only 2D substrates. Green fluorescent protein expressing human umbilical vein endothelial cells (GFP-HUVEC) were seeded onto the surface of the collagen gel filled CCR. The cells readily spread and grew in the chamber showing little to no cytotoxicity. Moreover, the cells remained segregated to the CCR demonstrating the spatial control in conjugating various chemistries to the CCR (FIG. 12A-12B).

Equipped with this functionality, a 3D vascular co-culture model could be achieved in the CCR inset. Human aortic smooth muscle cells (AoSMC) were embedded in a collagen gel matrix formed in the CCR and following gelation GFP-HUVECs were seeded on top of the gel (FIGS. 13A-13C). Because the chamber is PDMS, the CCR can be excised from the chamber and sectioned for histological analysis with little difficulty enabling cross-sectional analyses of cellular invasion or development in 3D matrices after mechanical stimulation. The MechanoBioTester can support numerous surface functionalities, matrix architectures, and cell types for their study under applied decoupled combinations of mechanical stimulation.

4. Discussion

The MechanoBioTester is a cell culture model for the systematic analysis of complex microenvironments. The system decouples mechanical stimuli to enable the independent control of flow regime, fluid shear stress, unidirectional cyclic stretch, hydrostatic pressure, and material properties. Many models use different principles to achieve the same applied mechanical stimulus (cone-and-plate viscometer versus parallel-plate flow chamber), which introduces variability between experiments and these devices in general are designed for one mechanical stimulus. The MechanoBioTester was designed to reduce this variability and serve as a complete system for many mechanobiology studies.

The chamber geometry was designed to decouple fluid flow from cyclic stretch. By recognizing the fluid flow negligibly affected the cyclic stretch mechanism while at the same time the cyclic stretch significantly affected the fluid flow mechanism, the system was designed to be closed for stretch and open for flow. In this way, the stretching parameters (magnitude and frequency) are first set and the flow rate is then modulated to compensate for the variability in flow rate induced by the chamber stretching. By using the volume of fluid in the flow circuit tubing, the hydrostatic pressure could be varied independent of the fluid flow and stretching by simply raising or lowering a media reservoir in relation to the chamber. Together this achieved, a defined region in the chamber, the CCR, in which the effects of fluid flow, cyclic stretch, and hydrostatic pressure could be well-defined and independently-controlled.

By separating the chamber construction material from that of the cell culture material, the system gained material-independence meaning this device is not exclusive to a single material. A suite of diverse biomaterials have been filled and bonded to the CCR: polydimethylsiloxane elastomer, polyacrylamide gel, poly(1,8-octanediol citrate), and type I collagen gel. Collectively, these materials cover a broad range of applications and mechanical properties relevant to physiological and pathological conditions. Moreover, any material with a stiffness less than that of the chamber (~1.5 MPa) and capable of sufficient bonding to PDMS is able to be used for stretching. Other biomaterials such as alginate and hyaluronic acid hydrogels may be sufficiently bonded to the CCR using the appropriate chemistries. For these materials it is proposed to first treat the PDMS with (3-aminopropyl)triethoxysilane (APTES) to put a primary amine group at the surface of the PDMS after which then use a carbodiimide crosslinker to link to the carboxylic acid groups on the alginate and hyaluronic acid hydrogels. In a similar manner, silk fibroin and poly(ethylene glycol) (PEG) hydrogels could be bonded to the CCR by first using APTES to put primary amines at their hydroxyl groups and then using sulfo-SANPAH to conjugate them to the PDMS surface as it has been shown for other primary amine containing species. A benefit of the MechanoBioTester is its versatility. For instance, if stretching is not of interest then the stiffness and PDMS bonding requirements are unnecessary—the device is still available for investigations concerned with fluid flow, hydrostatic pressure, and material. All combinations are able to be systematically varied giving it the ability to tease out the specific effects of different mechanical stimuli.

The system is straight forward to fabricate and use—cast it, fill it, seal it, test it. The PDMS chamber halves are first cast. The CCR is then treated with the appropriate conjugation chemistry to bond the CCR filler material of interest. Next, the CCR is filled with the desired experimental material, treated for cell adhesion if necessary, both halves are then joined and sealed together to form the complete chamber. The chamber is then filled with a cell suspension and kept in a cell culture incubator to allow cells to adhere to the CCR. After cell attachment, the chamber is rinsed and filled with fresh media. The chamber is then ready to be connected to the system to enable flow, stretch, and/or pressure stimulation. The devices for such stimulation are modular, open components and are controlled using open, inexpensive electronics (Arduino microcontrollers). This reduces the overall device cost and enables the investigator to easily modify system components for their specific studies. Even though the MechanoBioTester is a simple system, it was designed to enable complex analyses. Because the chamber is optically transparent it enables in situ live-cell imaging capabilities by using mobile fluorescent imaging technologies such as USB fluorescence microscopes or by transferring the chamber to a conventional inverted fluorescence microscope. Additionally, the optically transparent chamber enables photoactive (PEG) materials to be investigated during mechanical stimulation empowering the study of dynamic material systems[8,43,44]. Moreover, the system is medium throughput. Each chamber has two CCRs (top and bottom), which can be used to test different material conditions or act as experimental replicates. Because the chamber is compact and self-enclosed, multiple chambers can be connected to a single system by using a multichannel pump head and by stacking the chambers in the chamber stretcher. Furthermore, the chambers are robust because of the multistep sealing process, which enables the chambers to be transported with ease to conduct analyses using equipment in other lab spaces, buildings, or institutions. The bioreactor system supports multifaceted experimentation in a simple package.

The MechanoBioTester system can be improved. Despite being simple to fabricate, the entire fabrication process can be lengthy. The time to prepare a complete chamber can take anywhere from 2 to 3 days with our current methods depending on the complexity of the experiment. Because of this, different biocompatible silicone formulations for sealing the chamber halves have been investigated. Using ReproRubber® Thin Pour silicone, fabrication time can be significantly reduced from days to hours for PDMS and collagen filled CCRs. PA and POC filled CCRs require additional fabrication time because of the additional steps needed during their polymerization process. In addition, the chambers are single-use requiring new chambers to be fabricated for every experiment. To reduce the environmental footprint and operating cost of the system, methods for cleaning and sterilizing waste chambers to be reused in later experiments can be developed and optimized. For instance, PDMS filled CCR chambers could potentially be used multiple times after sufficient rinsing and sterilization steps[21]. It is necessary to note that PDMS has its own limitations being known to absorb small, hydrophobic molecules and leach uncured oligomer both of which can unduly influence cultured cells when left unaddressed[45,46]. To overcome this process, coatings and other chamber construction materials can be utilized. In terms of stimulation, the MechanoBioTester is confined to unidirectional cyclic stretch limiting the device's ability to investigate the combined effects of multidirectional cyclic stretch with the other stimuli[47]. Additionally, the fluid flow and cyclic stretch are only decoupled to support their constant value conditions i.e. a constant cyclic stretch value paired with a constant WSS value. Investigations requiring more dynamic stretching and flow conditions would require further simulation to determine their new fluid-structure interaction. Future versions of the device aim to address these concerns to ever improve the functionality of the system.

5. Conclusion

Described herein is the MechanoBioTester, an embodiment of a cell culture model system specially designed for decoupling mechanical stimuli for their independent control and systematic testing. The MechanoBioTester can allow investigation of complex microenvironments. By decoupling and supporting independent control of mechanical stimuli, the interrelatedness, and non-linear interactions between these stimuli to affect cellular behavior can continue to be understood. And it supports the study of this in 3D, co-culture settings giving a more complete model of the in vivo microenvironment using an in vitro platform. It also can be used as a material and chemical biocompatibility screening tool. By being material-independent, the CCR can be filled with newly synthesized biomaterials to quickly investigate the cellular response to the material in a more physiologically-relevant model—one with multiple forms of mechanical stimulation. Likewise, drug toxicity can be mechanically mediated and thus, the MechanoBioTester is apt to be a platform for studying chemo-mechanical microenvironmental interactions to aid in drug discovery[19,48,49]. An example of use is to utilize this system in the context of vascular mechanobiology; specifically, targeting combinations of wall shear stress, cyclic stretch, hydrostatic pressure, and substrate stiffness to understand how each component affects the regulation of mechanoresponsive pathways in endothelial cells and vascular smooth muscle cells. This cell culture model will not only allow the investigation of the main effects of these stimuli, but also their interactive effects. Mechanical stimuli exist in every part of the body and other groups may be interested in using the MechanoBioTester for studying the mechanobiology of other tissue-specific cells (osseous, chondrous, vascular, cardiac, lymphatic, pulmonary, and cancerous) with decoupled mechanic stimuli. The MechanoBioTester is a next generation system for studying mechanobiology and complex microenvironments in vitro.

Example 2

FIG. 30 is a flowchart of an embodiment of a method 100 of casting a bioreactor chamber is described herein. First, the top and bottom halves are cast with polymer in respective molds 101. The cell culture region of the flow chamber of the bottom half is then treated with conjugation chemistry of interest 103. Cell culture region filler of interest is then added to the treated cell culture region 105. The top and bottom halves are then joined 107 and sealed 109. The cell culture region can optionally be treated for cell adhesion if necessary between 105 and 107.

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

Embodiments of the present disclosure will employ, unless otherwise indicated, techniques of separating, testing, and constructing materials, which are within the skill of the art. Such techniques are explained fully in the literature.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

The invention claimed is:

1. A single-plate symmetrical bioreactor chamber comprising:
   a flow channel extending along a first axis, wherein the flow channel comprises an inlet and an outlet at opposing ends of the flow channel;
   a pair of struts on opposing ends of a second axis, wherein the second axis is substantially perpendicular to the first axis, wherein each strut of the pair of struts are placed on opposing sides of the flow channel, wherein the struts are configured to be coupled to a bi-directional linear actuator and configured to provide a strain perpendicular to a fluid flow through the flow channel, wherein the strain does not laterally displace cells present in the flow channel; and
      wherein the bi-directional linear actuator comprises a bi-directional lead screw configured to translate each strut of the pair of struts in opposite directions upon rotation of the bi-directional lead screw.

2. The single-plate symmetrical bioreactor chamber of claim 1, wherein at least a portion of the bioreactor chamber is composed of a stretchable material.

3. The single-plate symmetrical bioreactor chamber of claim 1, wherein the at least a portion of the bioreactor chamber is composed of a silicone rubber.

4. The single-plate symmetrical bioreactor chamber of claim 1, wherein at least a portion of the bioreactor chamber is optically translucent.

5. The single-plate symmetrical bioreactor chamber of claim 1, wherein the bioreactor chamber is configured to generate a cyclical strain to the flow channel.

6. The single-plate symmetrical bioreactor chamber of claim 1, further comprising a cell growth substrate.

7. The single-plate symmetrical bioreactor chamber of claim 6, further comprising a cell growth matrix.

8. The single-plate symmetrical bioreactor chamber of claim 7, wherein the cell growth matrix is one or more of silicones, polyacrylamides, collagen gels, fibronectins, poly (diol citrates), alginates, polyethylene glycol hydrogels, polyhydroxyalkanoates, hyaluronic acid hydrogels, or polyacrylic acids, individually or in combination.

9. The single-plate symmetrical bioreactor chamber of claim 7, wherein the cell growth matrix is a biomolecule matrix.

10. A bioreactor system comprising:
a single-plate symmetrical bioreactor chamber comprising a flow channel extending along a first axis, wherein the flow channel comprises an inlet and an outlet at opposing ends of the flow channel, and
wherein the bioreactor chamber further comprises a pair of struts on opposing ends of a second axis, wherein the second axis is substantially perpendicular to the first axis, wherein each strut of the pair of struts are placed on opposing sides of the flow channel, wherein the struts are configured to be coupled to a bi-directional linear actuator and configured to provide a strain perpendicular to a fluid flow through the flow channel, wherein the strain does not laterally displace cells present in the flow channel;
a fluid flow circuit, wherein the fluid flow circuit is fluidly coupled to the flow channel of the bioreactor chamber;
a bi-directional linear actuator, wherein the bidirectional linear actuator is coupled to the pair of struts of the bioreactor chamber;
a control system, wherein the control system is physically coupled, electrically coupled, and/or otherwise in communication with the bioreactor chamber, the fluid flow circuit, and/or the linear actuator.

11. The bioreactor system of claim 10, further comprising a hydrostatic pressure linear actuator, wherein the hydrostatic pressure linear actuator is fluidly coupled to the fluid flow circuit and physically coupled, electrically coupled, and/or otherwise in communication with the control system.

12. The bioreactor system of claim 10, wherein at least a portion of the bioreactor chamber is composed of a stretchable material.

13. The bioreactor system of claim 10, wherein at least a portion of the bioreactor chamber is optically transparent.

14. The bioreactor system of claim 10, wherein the bioreactor chamber is configured to generate a cyclical strain to the flow channel.

15. The bioreactor system of claim 10, wherein the bioreactor chamber further comprises a cell growth substrate.

16. The bioreactor system of claim 15, wherein the bioreactor chamber comprises top and bottom halves, wherein the cell growth substrate is coupled between the top and bottom halves of the bioreactor chamber.

17. A method of operating a bioreactor system, comprising:
providing a bioreactor system of claim 10;
immobilizing cells within the fluid flow channel of the bioreactor chamber;
applying a fluid flow in a first direction along a first axis;
simultaneously pulling both struts in opposite directions away from each other and in a direction along a second axis to apply a strain to the immobilized cells, wherein the second axis is substantially perpendicular to the first axis, wherein the cells are not laterally displaced along the second axis.

18. The method of claim 17, wherein the linear actuator simultaneously pulls both struts.

19. The method of claim 17, wherein the cells are immobilized on the cell growth substrate.

* * * * *